US011874215B2

(12) United States Patent
Li

(10) Patent No.: US 11,874,215 B2
(45) Date of Patent: Jan. 16, 2024

(54) ANALYZER AND DETECTION SYSTEM

(71) Applicant: BOE TECHNOLOGY GROUP CO., LTD., Beijing (CN)

(72) Inventor: Hongquan Li, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 104 days.

(21) Appl. No.: 17/617,472

(22) PCT Filed: Nov. 12, 2020

(86) PCT No.: PCT/CN2020/128373
§ 371 (c)(1),
(2) Date: Dec. 8, 2021

(87) PCT Pub. No.: WO2021/098581
PCT Pub. Date: May 27, 2021

(65) Prior Publication Data
US 2022/0236166 A1     Jul. 28, 2022

(30) Foreign Application Priority Data

Nov. 22, 2019  (CN) .......................... 201911158197.0
Apr. 30, 2020  (CN) .......................... 202010363715.9

(51) Int. Cl.
*G01N 21/01*     (2006.01)
*H04W 4/38*      (2018.01)
*G01N 33/02*     (2006.01)

(52) U.S. Cl.
CPC ............. *G01N 21/01* (2013.01); *G01N 33/02* (2013.01); *H04W 4/38* (2018.02)

(58) Field of Classification Search
CPC .... G01N 21/01; G01N 33/02; G01N 21/8483; G01N 21/274; G01N 21/81; G01N 2021/0112; G01N 2021/3181; G01N 2201/0221; G01N 2201/064; G01N 2201/1211; G01N 2201/1214;
(Continued)

(56) References Cited

U.S. PATENT DOCUMENTS 10,307,754 B2   6/2019   Bau-Madsen et al.
11,009,457 B2   5/2021   Morita et al.
(Continued)

FOREIGN PATENT DOCUMENTS

CN      101644667 A      2/2010
CN      104849222 A      8/2015
(Continued)

OTHER PUBLICATIONS

Search Report issued for EP Application No. 20888839.6, dated Dec. 13, 2022, 19 pages.

*Primary Examiner* — Md M Rahman
(74) *Attorney, Agent, or Firm* — Dave Law Group LLC; Raj S. Dave

(57) ABSTRACT

An analyzer and a detection system are provided. The analyzer includes a chip placement structure and at least one detector unit. The chip placement structure is configured to place a detection chip, and the detection chip is provided with at least one detection area. The at least one detector unit is configured to detect one or more detection areas of the detection chip in a case where the detection chip is placed on the chip placement structure.

16 Claims, 11 Drawing Sheets

(58) Field of Classification Search
CPC .. G01N 21/31; H04W 4/38; B01L 2300/0803; B01L 2300/0825; B01L 2300/126; B01L 3/502715; B01L 3/50273
USPC .......................................................... 356/244
See application file for complete search history.

(56) References Cited

U.S. PATENT DOCUMENTS

| | | | |
|---|---|---|---|
| 2003/0119202 A1 | 6/2003 | Kaylor et al. | |
| 2006/0240541 A1 | 10/2006 | Petruno et al. | |
| 2011/0031402 A1 | 2/2011 | Huttmann et al. | |
| 2011/0170092 A1 | 7/2011 | Uto et al. | |
| 2013/0050227 A1* | 2/2013 | Petersen | H01L 23/057 257/66 |
| 2015/0021326 A1* | 1/2015 | Giraud | A61J 1/03 220/254.1 |
| 2016/0370917 A1* | 12/2016 | Li | G06F 3/0443 |
| 2017/0115211 A1 | 4/2017 | Morimoto et al. | |
| 2018/0235560 A1* | 8/2018 | Suuronen | A61B 6/4452 |
| 2019/0035220 A1* | 1/2019 | deWaal | G07F 17/3227 |
| 2021/0346891 A1* | 11/2021 | Geng | G01K 1/026 |
| 2021/0354128 A1* | 11/2021 | Meng | G01N 21/255 |
| 2022/0357307 A1* | 11/2022 | Qin | G01N 21/27 |

FOREIGN PATENT DOCUMENTS

| | | | | |
|---|---|---|---|---|
| CN | 104931440 A | 9/2015 | | |
| CN | 204903388 U | 12/2015 | | |
| CN | 106662522 A | 5/2017 | | |
| CN | 109632657 A | 4/2019 | | |
| CN | 208833653 U | 5/2019 | | |
| CN | 211014324 U | 7/2020 | | |
| CN | 211553735 U | 9/2020 | | |
| CN | 211905402 U | 11/2020 | | |
| DE | 102007014034 B3 * | 9/2008 | ............ | E05F 15/443 |
| EP | 1508797 A1 | 2/2005 | | |
| JP | 2014145643 A | 8/2014 | | |
| JP | 2018059774 A | 4/2018 | | |
| WO | 2019044969 A1 | 3/2019 | | |

\* cited by examiner

ANALYZER AND DETECTION SYSTEM

CROSS-REFERENCE TO RELATED APPLICATIONS

The present application is the U.S. National Stage Entry of PCT/CN2020/128373 filed on Nov. 12, 2020, which claims priority to the Chinese Patent Application No. 201911158197.0, filed on Nov. 22, 2019, and Chinese Patent Application No. 202010363715.9 filed on Apr. 30, 2020, the entire disclosures of which are incorporated herein by reference as part of the disclosure of this application.

TECHNICAL FIELD

Embodiments of the present disclosure relate to an analyzer and a detection system.

BACKGROUND

In recent years, with the improvement of living standards, broad masses of people's requirements for balanced nutritional diet is higher and higher, especially for infants who take breast milk as the main source of nutrition, whose the nutrition balance is particularly important. The contents of trace elements in the breast milk, such as calcium, zinc, iron, lactose, and protein, can be detected, according to the test results, and mothers can be given proper nutrition and dietary guidance.

SUMMARY

Embodiments of the present disclosure provide an analyzer and a detection system. The analyzer can detect contents of various substances in the liquid to be detected in the detection chip during detection process.

At least one embodiment of the present disclosure provides an analyzer, including: a chip placement structure and at least one detector unit. The chip placement structure is configured to place a detection chip, wherein the detection chip is provided with at least one detection area. The at least one detector unit is configured to detect one detection area or more detection areas of the detection chip in a case where the detection chip is placed on the chip placement structure.

For example, in the analyzer provided by at least one embodiment of the present disclosure, the at least one detector unit includes at least one photoelectric detector unit.

For example, in the analyzer provided by at least one embodiment of the present disclosure, each of the at least one photoelectric detector unit includes at least one light-emitter element and at least one photoelectric sensor device.

For example, the analyzer provided by at least one embodiment of the present disclosure includes an optical path component, the optical path component is provided between the chip placement structure and the detector unit, and the optical path component is configured to transmit light emitted by the at least one light-emitter element to the chip placement structure and transmit light reflected from the detection chip placed on the chip placement structure to the at least one photoelectric sensor device.

For example, in the analyzer provided by at least one embodiment of the present disclosure, the optical path component includes a light splitter disk, the light splitter disk includes at least one group of light through holes, and the at least one group of light through holes corresponds to the at least one photoelectric detector unit respectively, each group of the at least one group of light through holes includes at least one light-emitting through hole and at least one light-reflecting through hole, the at least one light-emitting through hole allows the light emitted by the at least one light-emitter element of corresponding photoelectric detector unit to pass through, and the at least one light-reflecting through hole allows the light reflected from the detection chip placed on the chip placement structure to pass through so as to transmit to the at least one photoelectric sensor device of the corresponding photoelectric detector unit.

For example, in the analyzer provided by at least one embodiment of the present disclosure, at least one light through hole in each group of the at least one group of light through holes includes a rectangular hole or a circular hole.

For example, in the analyzer provided by at least one embodiment of the present disclosure, the at least one light-emitting through hole includes a rectangular hole, and the at least one light-reflecting through hole includes a circular hole.

For example, in the analyzer provided by at least one embodiment of the present disclosure, at least a portion of a side wall of at least one light through hole in each group of the at least one group of light through holes includes an inclined surface with respect to an axial direction of the light splitter disk.

For example, in the analyzer provided by at least one embodiment of the present disclosure, at least one side wall of the rectangular hole includes an inclined surface with respect to an axial direction of the light splitter disk.

For example, in the analyzer provided by at least one embodiment of the present disclosure, at least one side wall, extending in a radial direction of the light splitter disk, of the at least one light-emitting through hole includes an inclined surface.

For example, in the analyzer provided by at least one embodiment of the present disclosure, two side walls, extending in a radial direction of the light splitter disk, of the at least one light-emitting through hole include inclined surfaces with respect to an axial direction of the light splitter disk, and inclination directions of the inclined surfaces of the two side walls are different from each other.

For example, in the analyzer provided by at least one embodiment of the present disclosure, a value range of an inclined angle between the inclined surface where at least one side wall of the at least one light-emitting through hole is located and a direction perpendicular to an axial direction of the light splitter disk is from 130 degrees to 140 degrees.

For example, in the analyzer provided by at least one embodiment of the present disclosure, an opening of the at least one light-emitting through hole on a side facing away from the at least one photoelectric detector unit is larger than an opening of the at least one light-emitting through hole at a side close to the at least one photoelectric detector unit.

For example, in the analyzer provided by at least one embodiment of the present disclosure, at least one side wall of the at least one light-reflecting through hole includes an inclined surface with respect to an axial direction of the light splitter disk.

For example, in the analyzer provided by at least one embodiment of the present disclosure, a value range of an inclined angle between the inclined surface where the at least one side wall of the at least one light-reflecting through hole is located and a direction perpendicular to the axial direction of the light splitter disk is from 115 degrees to 125 degrees.

For example, in the analyzer provided by at least one embodiment of the present disclosure, the light splitter disk is provided to be center-symmetrical, and each group of the at least one group of light through holes is further provided to be center-symmetrical.

For example, in the analyzer provided by at least one embodiment of the present disclosure, a shape of the light splitter disk includes a circular shape, the at least one group of light through holes includes a plurality of groups of light through holes, and the plurality of groups of light through holes are evenly distributed in a circle shape around a center of the light splitter disk.

For example, in the analyzer provided by at least one embodiment of the present disclosure, each group of the at least one group of light through holes includes two light-emitting through holes and one light-reflecting through hole, and the two light-emitting through holes are provided at two opposite sides of the one light-reflecting through hole.

For example, in the analyzer provided by at least one embodiment of the present disclosure, the two light-emitting through holes are symmetrically provided at the two opposite sides of the one light-reflecting through hole.

For example, in the analyzer provided by at least one embodiment of the present disclosure, a linear distance between centers of two adjacent light-emitting through holes ranges from 5 mm to 8 mm, and a linear distance between a center of one of the two light-emitting through holes in each group of the at least one group of the light through holes and a center of the one light-reflecting through hole ranges from 2.5 mm to 4 mm.

For example, in the analyzer provided by at least one embodiment of the present disclosure, a linear distance between centers of two adjacent light-emitting through holes ranges from 5 mm to 8 mm, and a linear distance between a center of a light-emitting through hole in each group of the at least one group of the light through holes and a center of a nearest adjacent light-reflecting through hole ranges from 2.5 mm to 4 mm.

For example, in the analyzer provided by at least one embodiment of the present disclosure, the light splitter disk further includes a limiter structure, and the limiter structure is provided at an edge of the light splitter disk, and the limiter structure extends into the chip placement structure.

For example, in the analyzer provided by at least one embodiment of the present disclosure, the one light-reflecting through hole of each group of the at least one group of the light through holes includes a first reflecting through sub-hole located at a side of the light splitter disk facing away from the at least one detector unit and a second reflecting through sub-hole located at a side of the light splitter disk close to the at least one detector unit.

For example, in the analyzer provided by at least one embodiment of the present disclosure, a diameter of the first reflecting through sub-hole is smaller than a diameter of the second reflecting through sub-hole.

For example, in the analyzer provided by at least one embodiment of the present disclosure, a surface of the light splitter disk at a side facing away from the at least one detector unit includes at least one protrusion, and the at least one protrusion protrudes obliquely to the side facing away from the at least one detector unit along a direction from a side of the two light-emitting through holes of each group of the at least one group of light through holes close to the one light-reflecting through hole to a side close to the one light-reflecting through hole, and the one light-reflecting through hole of the at least one group of the light through holes is located in the at least one protrusion in a one-to-one correspondence, so that the protrusion shields light emitted from the at least one light-emitter element of corresponding photoelectric detector unit through the light-emitting through hole.

For example, in the analyzer provided by at least one embodiment of the present disclosure, each of the at least one protrusion is in a ring shape, and each of the at least one protrusion surrounds the one light-reflecting through hole of each group of the at least one group of light through holes.

For example, in the analyzer provided by at least one embodiment of the present disclosure, a value of a slope angle of the protrusion with respect to a direction perpendicular to an axial direction of the light splitter disk ranges from 130 degrees to 140 degrees, and a value range of a height of the protrusion protruding from the one light-reflecting through hole is from 0.4 mm to 0.6 mm.

For example, in the analyzer provided by at least one embodiment of the present disclosure, each of the at least one photoelectric detector unit includes two light-emitter elements and one photoelectric sensor device, and the two light-emitter elements are provided at two opposite sides of the one photoelectric sensor device; the two light-emitting through holes respectively allow the light emitted by the two light-emitter elements to pass through respectively, and the one light-reflecting through hole allows the light reflected from the detection chip placed on the chip placement structure to pass through so as to transmit to the one photoelectric sensor device.

For example, in the analyzer provided by at least one embodiment of the present disclosure, a linear distance between centers of two adjacent light-emitter elements ranges from 5 mm to 8 mm, and a linear distance between a center of one of the two light-emitter elements in a same photoelectric detector unit and a center of the one photoelectric sensor device ranges from 2.5 mm to 4 mm.

For example, in the analyzer provided by at least one embodiment of the present disclosure, a linear distance between centers of two adjacent light-emitter elements ranges from 5 mm to 8 mm, and a linear distance between a center of the light-emitter element in each of the at least one photoelectric detector unit and a center of a nearest adjacent photoelectric sensor device ranges from 2.5 mm to 4 mm.

For example, in the analyzer provided by at least one embodiment of the present disclosure, the at least one photoelectric detector unit includes a plurality of photoelectric detector units, and the plurality of the photoelectric detector units are provided in a row.

For example, the analyzer provided by at least one embodiment of the present disclosure further includes: a separator component. The separator component is provided between the optical path component and the chip placement structure, and the separator component includes a light-transmitter portion, and the light-transmitter portion is configured to allow light emitted by the at least one light-emitter element and light reflected from the detection chip placed on the chip placement structure to pass through.

For example, in the analyzer provided by at least one embodiment of the present disclosure, the light-transmitter portion of the separator component includes at least one transparent window, and the at least one transparent window respectively corresponds to the at least one detector unit to respectively allow the light emitted from the at least one light-emitter element of corresponding photoelectric detector unit and the light reflected from the detection chip placed on the chip placement structure to the at least one photoelectric sensor device of the corresponding photoelectric detector unit to pass through.

For example, in the analyzer provided by at least one embodiment of the present disclosure, the separator component further includes a substrate and at least one transparent sheet, the substrate includes at least one mounting through hole, and the at least one transparent sheet is embedded in the at least one mounting through hole to provide the at least one transparent window.

For example, the analyzer provided by at least one embodiment of the present disclosure further includes: a detection circuit board. The photoelectric detector unit is provided on the detection circuit board, and the detection circuit board includes a first positioning hole, the separator component includes a positioning pin and the light splitter disk includes a second positioning hole, or the separator component includes a second positioning hole and the light splitter disk includes a positioning column, and the positioning column penetrates both the first positioning hole and the second positioning hole to connect the light splitter disk, the separator component, and the detection circuit board.

For example, the analyzer provided by at least one embodiment of the present disclosure further includes: a rotation driver device, wherein the at least one detector unit includes one detector unit, and the rotation driver device is configured to drive the one detector unit to rotate with respect to the chip placement structure.

For example, in the analyzer provided by at least one embodiment of the present disclosure, the detection chip is further provided with a calibration reaction area, and after the detection chip is placed on the chip placement structure and before the detection area of the detection chip is detected, one of the at least one detector unit is further configured to calibrate the calibration reaction area of the detection chip.

For example, the analyzer provided by at least one embodiment of the present disclosure further includes: a first shell and a second shell, wherein the at least one detector unit is provided in a space enclosed by the first shell and the second shell.

For example, in the analyzer provided by at least one embodiment of the present disclosure, the first shell further includes at least one supporter portion, and the at least one supporter portion is provided at a bottom of the first shell to provide a support for the first shell.

For example, in the analyzer provided by at least one embodiment of the present disclosure, the second shell is hinged with the first shell at a first side, the second shell is configured to be closed with the first shell at a second side to enclose the chip placement structure and is configured to be opened at the second side to expose the chip placement structure, and the first side is opposite to the second side.

For example, in the analyzer provided by at least one embodiment of the present disclosure, the first shell includes a first opening and closing sub-component provided at the second side, the second shell includes a second opening and closing sub-component provided at the second side, and the first opening and closing component and the second opening and closing sub-component are configured to be combined with each other to close the first shell and the second shell with each other and configured to be separated from each other to open the first shell and the second shell with each other.

For example, in the analyzer provided by at least one embodiment of the present disclosure, the second opening and closing sub-component includes a first locking tongue in a long strip shape and a second locking tongue in a long strip shape, the first locking tongue and the second locking tongue are provided side by side in a pair, the first opening and closing sub-component includes a groove and a locker, and the locker is located in the groove, a first end portion of the first locking tongue and a first end portion of the second locking tongue are configured to extend into the groove and to be snapped with the locker so that the first shell and the second shell are closed, and the first shell and the second shell are configured to be separated from the locker so that the first shell and the second shell are opened.

For example, in the analyzer provided by at least one embodiment of the present disclosure, the second opening and closing sub-component further includes an elastic component, the elastic component is provided at both a middle portion of the first locking tongue and a middle portion of the second locking tongue to elastically connect the first locking tongue and the second locking tongue, and the elastic component is configured to apply an elastic force to place the first locking tongue and the second locking tongue in a state of being snapped with the locker.

For example, in the analyzer provided by at least one embodiment of the present disclosure, the elastic component includes a torsion spring, the torsion spring is configured to apply an elastic force that allows the first end portion of the first locking tongue and the first end portion of the second locking tongue approach each other, the second opening and closing sub-component further includes a switch, the switch is connected with the first locking tongue and the second locking tongue, and the switch is configured to be operable to separate the first end portion of the first locking tongue and the first end portion of the second locking tongue from the locker in the state of being snapped with the locker.

For example, in the analyzer provided by at least one embodiment of the present disclosure, the second opening and closing sub-component further includes a connector component, and the connector component is provided in a middle portion of the first locking tongue, a surface of the connector component opposite to the second locking tongue is an inclined surface to form a limiter track, and the limiter track is configured to limit opening and closing angles of the first locking tongue and the second locking tongue.

For example, the analyzer provided by at least one embodiment of the present disclosure further includes: a displayer device, provided at the second shell.

For example, the analyzer provided by at least one embodiment of the present disclosure further includes: at least one micro-switch. The at least one micro-switch is connected in signal with the displayer device, and the at least one micro-switch is configured to control contents displayed on the displayer device.

For example, in the analyzer provided by at least one embodiment of the present disclosure, the at least one micro-switch includes two micro-switches, one micro-switch of the two micro-switches is provided at the first end portion of the first locking tongue and is configured to control a switch of the analyzer, the other micro-switch of the two micro-switches is provided at the first end portion of the second locking tongue and is configured to control display of detection results of the analyzer on the displayer device.

For example, the analyzer provided by at least one embodiment of the present disclosure further includes: a controller device, connected in signal with the detector unit and the displayer device, wherein the controller device is configured to receive detection results of the detector unit and send the detection results to the displayer device, and the displayer device is configured to display the detection results.

For example, the analyzer provided by at least one embodiment of the present disclosure further includes: a signal transmitter and receiver device. The signal transmitter and receiver device is connected with the controller device, and the signal transmitter and receiver device is configured to upload the detection results to a mobile device, or is configured to receive control signals from the mobile device and transmit the control signals to the controller device to control an operation of the analyzer.

For example, the analyzer provided by at least one embodiment of the present disclosure further includes: a temperature sensor and a humidity sensor. The temperature sensor and the humidity sensor are respectively connected with the controller device, the temperature sensor is configured to detect environmental temperature and to upload a temperature detection data to the controller device, and the humidity sensor is configured to detect environmental humidity and to upload a humidity detection data to the controller device.

At least one embodiment of the present disclosure further includes a detection system, including: the analyzer according to any one described above and a detection chip. The detection chip is configured to be placed on the chip placement structure of the analyzer.

At least one embodiment of the present disclosure further includes an analyzer, including: a detector module and a controller module. The detector module includes a chip placement structure, wherein the detector module is configured so that in a case where a detection chip provided with at least one detection area is placed on the chip placement structure, the at least one detection area of the detection chip is detected, and the controller module is configured to control a detection operation of the detector module and receive detection results of the detector module.

For example, in the analyzer provided by at least one embodiment of the present disclosure, the detector module includes at least one photoelectric detector unit.

For example, in the analyzer provided by at least one embodiment of the present disclosure, each of the at least one photoelectric detector unit includes at least one light-emitter element and at least one photoelectric sensor device.

For example, the analyzer provided by at least one embodiment of the present disclosure further includes: a light splitter component. The light splitter component is provided between the chip placement structure and the at least one photoelectric detector unit, and is configured to transmit light emitted by the at least one light-emitter element to the chip placement structure and to transmit light reflected from the detection chip placed on the chip placement structure to the at least one photoelectric sensor device.

For example, the analyzer provided by at least one embodiment of the present disclosure further includes: a separator component. The separator component is provided between the light splitter component and the chip placement structure, and the separator component includes a light-transmitter portion, the light-transmitter portion is configured to pass the light emitted by the at least one light-emitter element and the light reflected from the detection chip placed on the chip placement structure.

For example, the analyzer provided by at least one embodiment of the present disclosure further includes: a displayer module. The displayer module is connected in signal with the controller module, and the displayer module is configured to receive the detection results of the detector module sent by the controller module and to display the detection results.

For example, the analyzer provided by at least one embodiment of the present disclosure further includes: a switch module. The switch module is connected in signal with the displayer module, and is configured to control contents displayed on the displayer module.

For example, the analyzer provided by at least one embodiment of the present disclosure further includes: a signal transmitter and receiver device. The signal transmitter and receiver device is connected with the controller module, and is configured to upload the detection results of the detector module to the mobile device, and is configured to receive control signals from a mobile device and to transmit the control signals to the controller module to control the operation of the analyzer.

According to an analyzer and a detection system provided by at least one embodiment of the present disclosure, because the detector module includes at least one detector unit, the analyzer can detect contents of various substances in the liquid to be detected in the detection chip placed on the chip placement structure of the analyzer during detection process.

BRIEF DESCRIPTION OF THE DRAWINGS

In order to clearly illustrate the technical solution of the embodiments of the present disclosure, the drawings of the embodiments will be briefly described. It is obvious that the described drawings in the following are only related to some embodiments of the present disclosure and thus are not limitative of the present disclosure.

DETAILED DESCRIPTION

Figure 1A:
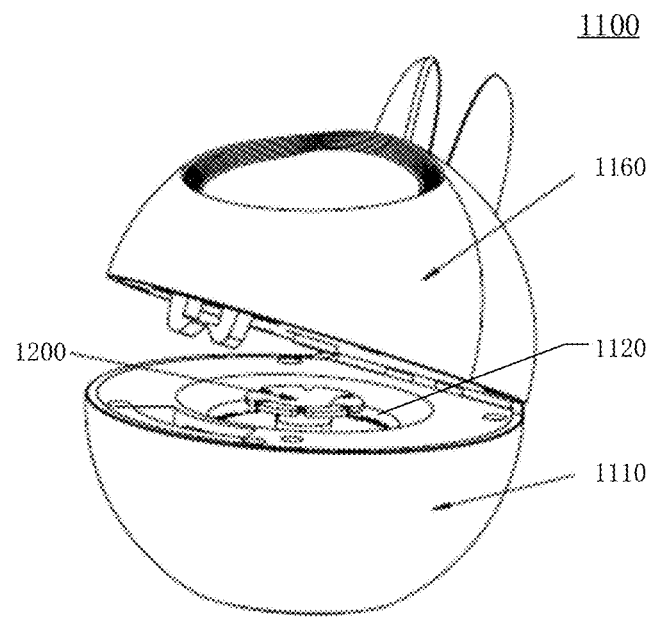
FIG. 1A is a schematic diagram of an analyzer provided by at least one embodiment of the present disclosure.

In order to make objectives, technical details, and advantages of the embodiments of the present disclosure apparent, the technical solutions of the embodiments will be described in a clearly and fully understandable way in connection with the drawings related to the embodiments of the present disclosure. Apparently, the described embodiments are just a part but not all of the embodiments of the present disclosure. Based on the described embodiments herein, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present disclosure belongs. The terms "first", "second", etc., which are used in the present disclosure, are not intended to indicate any sequence, amount or importance, but distinguish various components. Similarly, similar terms such as "a", "an", or "the", etc., do not indicate the limitation of quantity, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. For the convenience of description, "On," "under," and the like are given in some drawings only to indicate relative position relationship, and when the position of the described object is changed, the relative position relationship may be changed accordingly.

At present, An analytical equipment available in the market for detecting the substance content of various liquids, such as breast milk and milk, is mainly a large-scale testing equipment, the price of the large-scale testing equipment is high, the operation of the large-scale testing equipment is complicated, and special training is further required for operators. The above-mentioned testing equipment is mainly concentrated in hospitals or testing institutions, to provide substance content testing for those people in need. Therefore, some liquid need to be tested in the hospitals or the special testing institutions, the process is time-consuming and laborious, and for those people with testing requirements, regular testing is restricted. For liquid such as breast milk and milk that require frequent testing, it is particularly important to monitor the substance content regularly. Therefore, the inventor notices that providing an analyzer which is portable, compact, easy to operate, and can be used at home to detect the substance content of liquids, such as the breast milk, is of great significance.

A lab-on-a-chip refers to a technology that integrates or basically integrates basic operating units such as sample preparation, biological and chemical reactions, and separation detection into a chip, for example, with several square centimeters, for completing different biological or chemical reaction processes and analyzing products of above processes. The signal generated in the chip requires to be detected, and at present, the most commonly used detection methods include laser-induced fluorescence, mass spectrometry, ultraviolet, chemiluminescence, etc.

At least one embodiment of the present disclosure provides an analyzer and a detection system. The analyzer includes a first shell, a chip placement structure, and at least one detector unit. The chip placement structure is arranged in the first shell and is configured to place the detection chip, and the detection chip has at least one detection area. The at least one detector unit is arranged in the first shell, and the at least one detector unit is configured to detect one or more detection areas of the detection chip in the case where the detection chip is placed on the chip placement structure.

Because the detector module of the analyzer includes at least one detector unit, the analyzer can detect a plurality of detection areas of the detection chip during the detection process by the at least one detector unit, so that the contents of various substances in the liquid to be detected in the detection chip is detected.

Hereinafter, an analyzer and a detection system provided by one or more embodiments of the present disclosure will be described in detail with reference to the accompanying drawings.

For example, in some examples, FIG. 1A is a schematic diagram of an analyzer provided by at least one embodiment of the present disclosure. As shown in FIG. 1A, the analyzer 1100 includes a first shell 1110, a second shell 1160, and a chip placement structure 1120.

The chip placement structure 1120 is located in the first shell 1110, and is configured to place a detection chip 1200. The first shell 1110 and the second shell 1160 can be opened and closed at a side, which is convenient for users to place and retrieve the detection chip 1200, and avoid the interference of external light to the detection of the detection chip in the case where the analyzer 1100 is working. The analyzer 1100 further includes a detector unit, and the detector unit is located under the chip placement structure 1120 in the first shell 1110 to detect the substance content of the liquid to be detected in the detection chip 1200 placed on the chip placement structure 1120. In the process of using, after preparing the detection chip 1200 containing a test sample, by user first opens the first shell 1110 and the second shell 1160, places the detection chip 1200 on the chip placement structure 1120, and then closes the first shell 1110 and the second shell 1160. The analyzer 1100 can detect the substance content of the liquid to be detected in the detection chip 1200, and after that the detection is completed, detection results are output. Finally the user can open the first shell 1110 and the second shell 1160 again, and take out the detection chip 1200.

Figure 2:
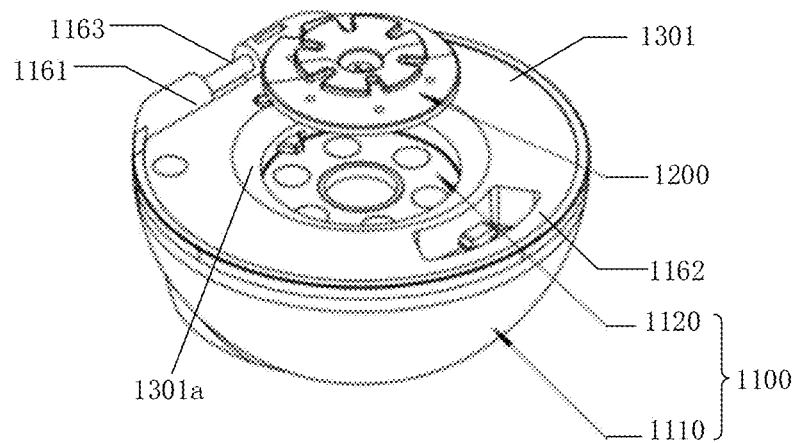
FIG. 2 is a structural schematic diagram of a lower portion of the analyzer provided by at least one embodiment of the present disclosure.
Figure 4A:
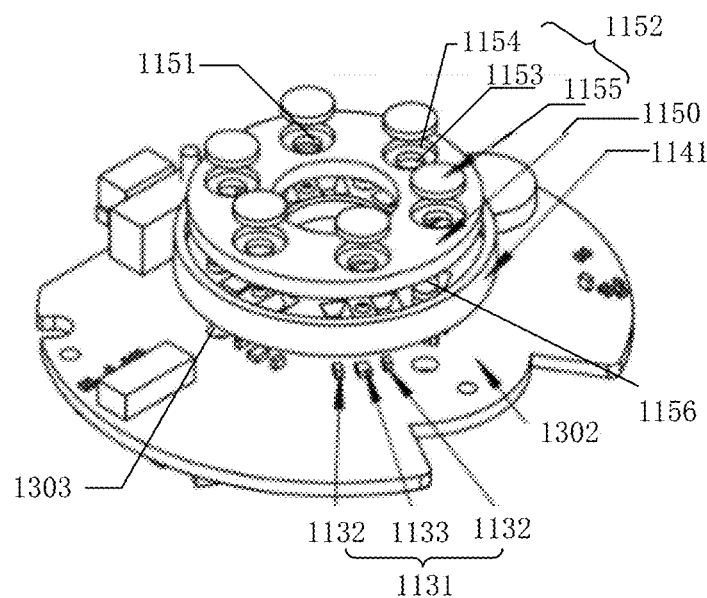
FIG. 4A is a structural schematic diagram of a detector module and an optical path component of the analyzer provided by at least one embodiment of the disclosure.
Figure 6A:
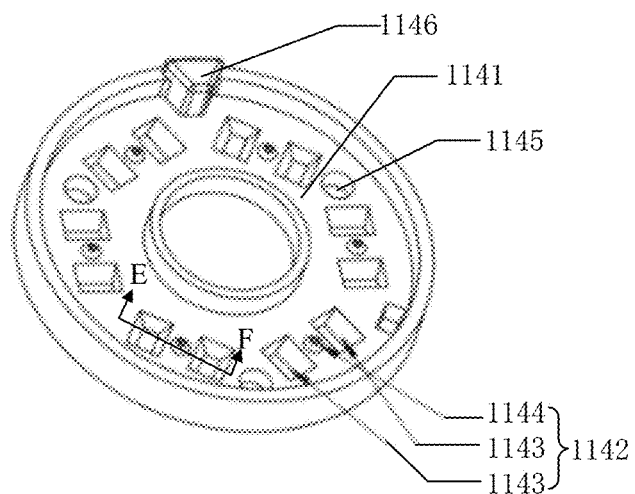
FIG. 6A is a structural schematic diagram of a light splitter disk of the analyzer provided by at least one embodiment of the present disclosure.

For example, in some examples, the chip placement structure 1120 is a lower "concave" accommodating space formed in the first shell 1110 from an opening (for example, a circular opening 1301a of the first shielding plate 1301 in FIG. 2) in the upper surface of the first shell 1110 (for example, formed by a surface of the first shielding plate 1301 in FIG. 2). For example, a cross section of the accommodating space is substantially in a circular shape. It should be noted that, the cross section can also be other shapes, such as a rectangular shape, an oval shape, etc. For example, as shown in FIG. 2, the chip placement structure 1120 is a space composed of the opening 1301a of the first shielding plate 1301, an inner sidewall of the light splitter disk 1141, and an upper surface (as shown in FIG. 6A) of a separator component 1150 (as shown in FIG. 4A). It should be noted that, the structure of the first shielding plate 1301, the light splitter disk 1141, and the separator component 1150 will be described in detail in the following.

For example, in other embodiments, the second shell 1160 of the analyzer 1100 can be removed, for example, the upper surface of the first shell 1110 is made into a plane that can shield light, an opening is arranged at a side surface of the first shell 1110, and the opening is communicated with the chip placement structure 1120. An object stage can be added on the chip placement structure 1120, the object stage can be ejected from the opening of the chip placement structure 1120 to place the detection chip 1200 on the object stage, and then the object stage is pushed into the chip placement structure 1120 to detect the detection chip 1200. It should be noted that, an operation of the object stage can be chosen to be a drawer type, and ambient light is shielded in the case where the detection chip 1200 is detected. The embodiments of the present disclosure is not limited by the shape and the structure of the second shell 1160.

For example, in other embodiments, the chip placement structure 1120 can also be configured as a plurality of cross beams erected on the opening 1301a of the first shielding plate 1301, and the detection chip 1200 can be directly placed on the beams. In addition, the beams can also be made of transparent material, or the positions of the beams are staggered from the detection areas of the detection chip 1200. For another example, a plurality of fulcrums may be arranged at the side wall of the chip placement structure 1120, the detection chip 1200 is arranged with a plurality of notches on the lower surface corresponding to the positions of the plurality of fulcrums. In the case where the detection chip 1200 is placed on the chip placement structure 1120, the plurality of fulcrums cooperate with the notches of the detection chip 1200 to stably place the detection chip 1200. For another example, a clamping mechanism may be arranged at the side wall of the chip placement structure 1120, the detection chip 1200 is stably placed in the chip placement structure 1120 by the clamping mechanism. For another example, the chip placement structure 1120 may also include a platform that can be raised and lowered to put the detection chip 1200 on the platform for detection. A carrying portion of the platform may include a transparent structure, or a light-transmitting structure (for example, a light through hole) is arranged in a portion corresponding to the detection areas of the detection chip 1200. It should be noted that, the detection chip 1200 in the present disclosure refers to a chip configured to integrate or substantially integrate of basic operating units such as sample preparation, biological and chemical reactions, and separation detection into a piece of, for example, several square centimeters. For example, the detection chip 1200 may include a microfluidic chip, which is configured to detect the substance content of the liquid to be detected.

Figure 1B:
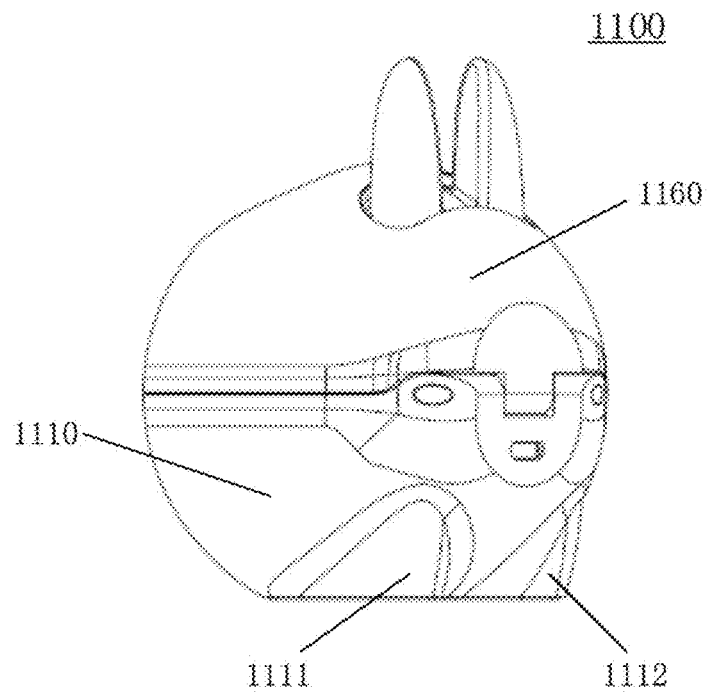
FIG. 1B is another schematic diagram of the analyzer provided by at least one embodiment of the present disclosure.

For example, in some examples, FIG. 1B is another schematic diagram of the analyzer provided by at least one embodiment of the present disclosure. As shown in FIG. 1B, the first shell 1110 includes a first supporter portion 1111 and a second supporter portion 1112. For example, the first supporter portion 1111 and the second supporter portion 1112 are arranged symmetrically with respect to a center line of the first shell 1110. The first supporter portion 1111 and the second supporter portion 1112 are arranged at the bottom of the first shell 1110, and for example, include supporting surfaces respectively. In this way, in the case where the analyzer is placed on the supporting surfaces, a stable support for the first shell 1110 on a plane is provided, and the first shell 1110 is prevented from tilting to cause a relative positional relationship between the internal structures of the analyzer 1100 to shift.

Figure 3:
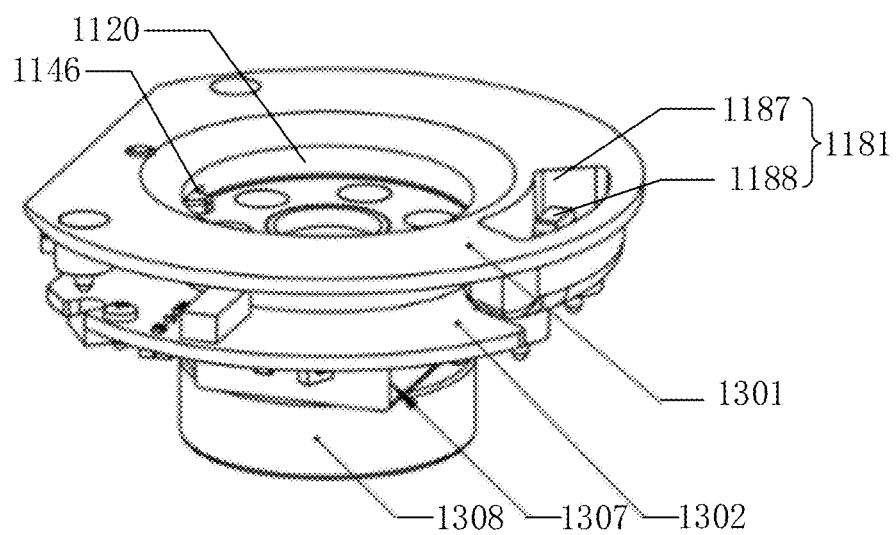
FIG. 3 is a schematic diagram of a partial structure of a lower portion of the analyzer provided by at least one embodiment of the present disclosure.

FIG. 2 is a structural schematic diagram of a lower portion of the analyzer provided by at least one embodiment of the present disclosure; FIG. 3 is a schematic diagram of a partial structure of a lower portion of the analyzer provided by at least one embodiment of the present disclosure; FIG. 4A is a structural schematic diagram of a detector module and an optical path component of the analyzer provided by at least one embodiment of the disclosure.

As shown in FIG. 2, FIG. 3, and FIG. 4A, the lower portion of the analyzer 1100 includes a first shell 1110 and a chip placement structure 1120. The detection chip 1200 includes a plurality of detection areas, and the detailed structure of the detection chip 1200 can refer to FIG. 12A, FIG. 12B, and FIG. 12C described in the following. In the examples in the figures, the chip placement structure 1120 provides a chamber for accommodating and supporting the detection chip 1200 and the chamber has substantially the same cross-sectional shape as the detection chip 1200. For example, a circular chamber is shown in the figures, the chip placement structure 1120 may also include a clamping structure to fix the inserted detection chip. For example, the clamping structure includes a limiter block, which is not limited in the embodiments of the present disclosure.

The lower portion of the analyzer 1100 further includes a detector unit for detecting the inserted detection chip 1200. The detector unit may include of various types, for example, including but not limited to photoelectric detector units. The detector unit is arranged in the first shell 1110. In the following descriptions, the photoelectric detector units are taken as an example for description. As shown in FIG. 4A, the detector unit includes at least one photoelectric detector units. The photoelectric detector unit may include of various types, for example, including but not limited to photoelectric detector units 1131. These photoelectric detector units 1131 are configured to detect the plurality of detection areas of the detection chip 1200 in the case where the detection chip 1200 is placed on the chip placement structure 1120, and specific exemplary descriptions are as follows. For example, a notch can be arranged in a circumferential direction of the detection chip 1200, and the shape of the notch is the same as the shape of the limiter block of the chip placement structure 1120, so that in the case where the detection chip 1200 is placed on the chip placement structure 1120, the notch of the detection chip 1200 is sleeved at the limiter block, and the detection areas of the detection chip 1200 and the photoelectric detector units 1131 are aligned in a direction perpendicular to the photoelectric detector units 1131, thereby allowing the user to place the detection chip 1200 on the chip placement structure 1120 more conveniently and accurately. The embodiments of the present disclosure may also adopt other alignment methods. For example, positioning marks or positioning springs are arranged on the chip placement structure 1120 to align with the detection chip 1200. The embodiments of the present disclosure are not limited to this.

In some embodiments, an outer surface of the first shell 1110 is approximately in a semi-spherical shape, the chip placement structure 1120 is located in the first shell 1110 close to the upper side of the first shell 1110 to facilitate the insertion of the detection chip. The chip placement structure 1120 includes a first shielding plate 1301, the first shielding plate 1301 is connected with the upper side of the first shell 1110, for example, by a method of snap connection, or a method of screw connection. An opening 1301a is arranged at a center of the first shielding plate 1301 to form a space for placing the detection chip 1200 in the first shell 1110 to provide an accommodation chamber. The first shielding plate 1301 can shield other stray light outside the first shell 1110 to avoid interference of other light rays on the detection result. For example, the accommodation chamber of the chip placement structure 1120 is in a cylindrical shape to match the shape of the detection chip 1200. The chip placement structure may also have other shapes, such as a quadrilateral shape, a polygonal shape, etc., which are not limited in the embodiments of the present disclosure.

For example, in other examples, the first shell 1110 may also have other shapes, such as a rectangular parallelepiped, etc., which are not limited in the embodiments of the present disclosure.

As shown in FIG. 4A, the lower portion of the analyzer 1100 further includes a detection circuit board 1302, the detection circuit board 1302 is arranged under the chip placement structure 1120 in the first shell 1110. The detector unit is arranged on the detection circuit board 1302 and corresponds to the detection chip 1200 in an axial direction of the first shell 1110. The detector unit includes a plurality of photoelectric detector units 1131, the plurality of photoelectric detector units 1131 respectively correspond to the plurality of detection areas of the detection chip in the axial direction of the first shell 1110.

For example, as shown in FIG. 4A, a plurality of photoelectric detector units 1131 are evenly arranged on a same circumference to respectively detect the plurality of detection areas of the detection chip 1200, for example, to detect the plurality of detection areas of the detection chip 1200 at the same time, or to detect the plurality of detection areas of the detection chip 1200 in a certain order, so that the contents of various substances in the liquid to be detected in the detection chip 1200 are detected. With the structure design that the plurality of photoelectric detector units 1131 are evenly arranged on the same circumference, the crosstalk of light can avoid in different photoelectric detector units, and the accuracy of optical detection can be realized.

It should be noted that, the plurality of detection areas of the detection chip 1200 are arranged on the same circumference, the plurality of corresponding photoelectric detector units 1131 are evenly arranged on the same circumference. In the case where the plurality of detection areas of the detection chip 1200 are arranged on the same circumference, and in the case where a sample is injected from the center of the detection chip 1200, sample injection distances of the plurality of detection areas are the same, so that uniform sample injection can be achieved.

For example, in other embodiments, the plurality of photoelectric detector units 1131 can also be evenly arranged on vertices of a regular polygonal shape, so that the sample injection distances of the plurality of detection areas of the corresponding detection chip are the same. Of course, without considering the sample injection distances of the detection areas of the detection chip, the plurality of photoelectric detector units 1131 can also be arranged in various shapes, for example, can be arranged in a row, or a matrix, etc. The embodiments of the present disclosure is not limited to the arrangement of the plurality of photoelectric detector units 1131.

For example, in some examples, each of the plurality of photoelectric detector units 1131 includes at least one light-emitter element and at least one photoelectric sensor device. In an example as shown in FIG. 4A, the plurality of photoelectric detector units 1131 respectively includes two photoelectric light-emitter elements 1132 and a photoelectric sensor device 1133. The two photoelectric light-emitter elements 1132 (for example, are symmetrical) are located at two sides of the photoelectric sensor device 1133. For example, a distance between two adjacent photoelectric light-emitter elements 1132 located in different photoelectric detector units 1131 is greater than a distance between the photoelectric light-emitter element 1132 and the photoelectric sensor device 1133 in a same photoelectric detector unit 1131, so that interference of light signals between different photoelectric detector units 1131 is avoided. The arrangement of two photoelectric light-emitter elements 1132 and one photoelectric sensor device 1133 can ensure that the light emitted by the light-emitter elements 1132 is evenly incident on the detection areas of the detection chip 1200, and the arrangement can also increase the intensity of the incident light provided by the two light-emitter elements 1132 and the intensity of the reflected light after being reflected by the detection chip 1200, and then the detection stability of the analyzer is improved.

For example, the distance between two adjacent light-emitter elements 1132 in different photoelectric detector units 1131, for example, a linear distance between centers of two adjacent light-emitter elements 1132 ranges from 5 mm to 8 mm. For another example, in FIG. 4A, the linear distance between the centers of two adjacent light-emitter elements 1132 is about 6 mm. For example, in the same photoelectric detector unit 1131, a linear distance between a center of one of the two light-emitter elements 1132 and a center of the photoelectric sensor device 1133 ranges from 2.5 mm to 4 mm. For another example, in FIG. 4A, the linear distance between the center of one of the two light-emitter elements 1132 and the center of the photoelectric sensor device 1133 is about 3 mm. For example, the distance between the centers of two adjacent photoelectric detector units 1131 on the circumference ranges from 10 mm to 15 mm. For another example, in FIG. 4A, the distance between the centers of two adjacent photoelectric detector units 1131 on the circumference is 12.5 mm. It should be noted that, the word "about" means that the value can be varied within, for example, ±15% of the value.

For example, in some examples, as shown in FIG. 4A, for example, the number of the plurality of photoelectric detector units 1131 is six. For another example, the number of the photoelectric detector units 1131 can also be two, three, four, five, seven, etc., the number is determined according to the number of detection areas of the detection chip 1200, and the embodiments of the present disclosure are not limited by the number of the plurality of photoelectric detector units 1131.

For example, in other examples, the plurality of photoelectric detector unit 1131 respectively may also include a photoelectric sensor device 1133 and a light-emitter element 1132, and the detection of the liquid to be detected in the detection area of the detection chip 1200 can also be realized. Alternatively, the photoelectric detector unit 1131 may also include a plurality of photoelectric sensor devices 1133 and a plurality of light-emitter elements 1132, the plurality of photoelectric sensor devices 1133 can detect different substances in the liquid to be detected. The embodiments of the present disclosure are not limited by the number of the light-emitter elements 1132 and the number of the photoelectric sensor devices 1133.

For example, the arrangements of the plurality of the photoelectric sensor devices 1133 and the plurality of the light-emitter elements 1132 of the photoelectric detector unit 1131 can be flexibly changed according to the requirements of the detection index of the liquid to be detected of the detection chip 1200. For example, the plurality of the light-emitter elements 1132 surround the photoelectric sensor device 1133 in a manner of providing the moon with stars, or the plurality of the light-emitter elements 1132 are arranged in two rows at both sides of the photoelectric sensor device 1133.

Figure 5A:
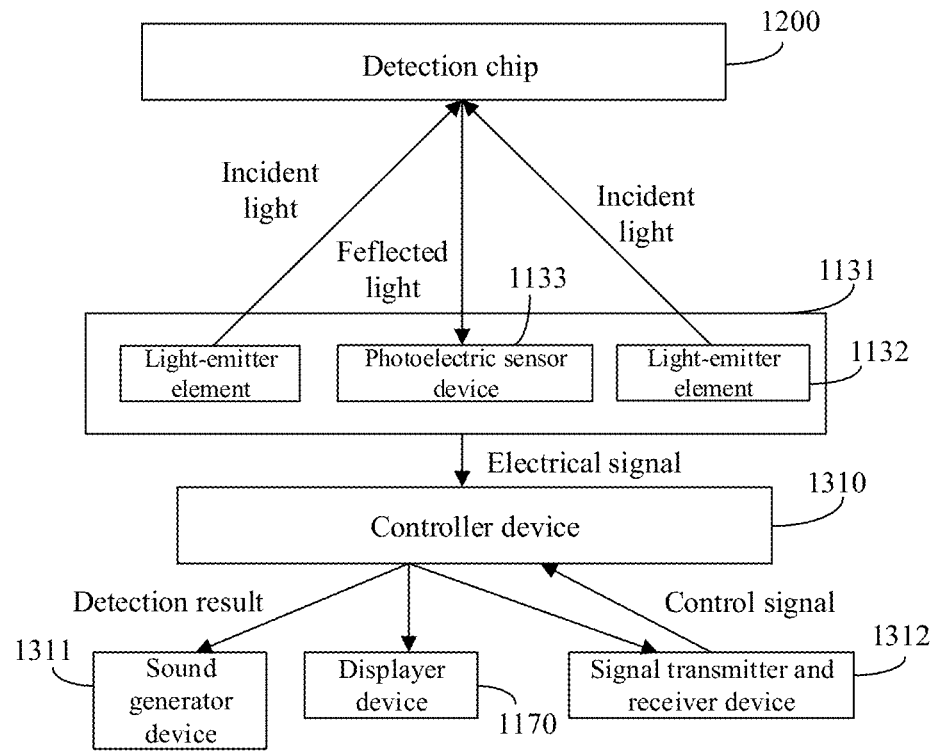
FIG. 5A is a schematic diagram of a detection principle of the analyzer provided by at least one embodiment of the present disclosure.

FIG. 5A is a schematic diagram of a detection principle of the analyzer provided by at least one embodiment of the present disclosure. As shown in FIG. 5A, the light-emitter elements 1132 are configured to generate light signals, a specific intensity light (incident light) emitted by the light-emitter elements 1132 is transmitted to the chip placement structure 1120 to reach the detection chip 1200 placed on the chip placement structure 1120, and then the light reflected by the detection areas (the detection sample in the detection chip 1200) of the detection chip 1200 is received by the photoelectric sensor device 1133. The photoelectric sensor device 1133 will receive light signals (reflected light), and convert the light signals into electrical signals. According to the electrical signals, the intensity of the light signals received by the photoelectric sensor device 1133 can be obtained.

For example, in other examples, the light-emitter element 1132 may also be arranged as one light-emitter element 1132, that is, the light emitted by the one light-emitter element 1132 illuminates the detection areas of the detection chip 1200 as incident light. The detection principle of the embodiment of the present disclosure is not limited by the number of the light-emitter elements 1132.

An absorbance value of the liquid to be detected is calculated according to the following formula:

$$A = \log \frac{I_0}{I} \quad (1)$$

In the above formula, $I_0$ is intensity of incident light of the detection chip, I is intensity of reflected light of the detection chip, and A is an absorbance value. The content of the specific substance in the liquid to be detected has a linear relationship with the absorbance value. The incident light of a certain wavelength is incident on the detection areas of the detection chip 1200, the liquid to be detected in the detection areas partially absorbs the light and then reflects the light, and the intensity of light absorbed has a linear relationship with the substance content of the liquid to be detected in a detection areas. After receiving the reflected light through the photoelectric sensor device 1133, an electrical signal are obtained, and the intensity of the reflected light can be obtained according to the magnitude of the electrical signal. The intensity of the reflected light and the intensity of the incident light are used to obtain the absorbance value by the formula (1).

For example, in some examples, the light-emitter elements 1132 and the photoelectric sensor device 1133 of the analyzer 1100 need to be calibrated to ensure the stability of the light source of the analyzer 1100. A standard gray scale plate is configured to calibrate the light emitted by the light-emitter elements 1132 of the analyzer 1100. The standard gray scale plate is placed on the chip placement structure, and the absorbance value of the standard gray scale plate to the incident light of the light-emitter elements is a known standard absorbance value. The absorbance value obtained, after that the analyzer 1100 detects the standard gray scale plate, is compared with the standard absorbance value, and the light emitted by the light-emitter elements 1132 of the analyzer 1100 is calibrated according to a comparison result.

Figure 5B:
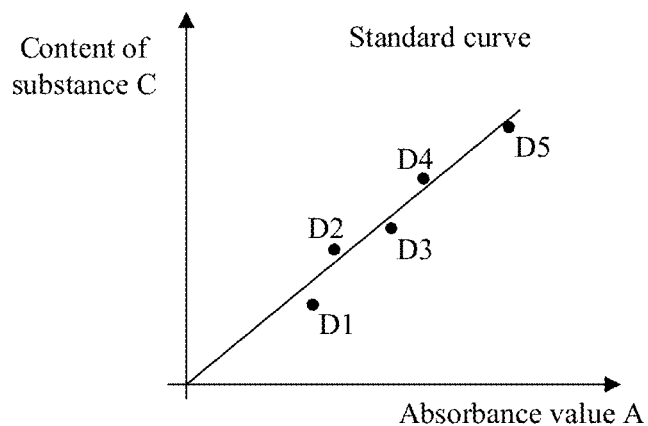
FIG. 5B is a schematic diagram of a standard curve of absorbance value and substance content of the analyzer provided by at least one embodiment of the disclosure.

For example, a liquid with a known substance type and a known content can be used as a calibration test sample, after the analyzer 1100 detects the absorbance value of the calibration test sample, the coordinate points of the absorbance value A and the content C of the substance is obtained as shown in FIG. 5B, for example, at points D1, D2, D3, D4 and D5, and there is a linear relationship between the absorbance value A and the substance content C. After performing a linear fitting based on the above five points, a standard curve of the absorbance value A and the substance content C is obtained. It should be noted that, the five points in FIG. 5B are just an example, a variety of test samples can be used to obtain multiple points to obtain a standard curve, the embodiments of the present disclosure are not limited to the specific process of obtaining the standard curve.

For example, in some examples, according to the absorbance value obtained by detecting the liquid to be detected by the analyzer, the absorbance value is brought into the standard curve of absorbance value A and substance content C as shown in FIG. 5B, and the content of the substance corresponding to the absorbance value of the liquid to be detected can be obtained. By separately detecting the liquid to be detected in the plurality of the detection areas of the detection chip 1200, the contents of various substances in the liquid to be detected are obtained.

For example, in some examples, the light-emitter elements 1132 include light-emitting diodes (LEDs), the photoelectric sensor devices 1133 include photo-diodes (PDs), such as silicon photo-diodes. The light-emitting diodes can emit light of specific wavelengths (for example, infrared light, red light, green light, etc.), the light-emitting diode of specific wavelengths can be selected according to the type of the substance to be detected. The wavelengths of light emitted by the light-emitting diodes located in different photoelectric detector units 1131 are different, so that detecting various substances can be realized by using the plurality of the photoelectric detector units 1131. For example, a photoelectric detector unit 1131 can select light-emitter elements that emit light with a wavelength of 630 nm, which is configured to detect the content of lactose and the content of fat in the liquid to be tested. A maximum absorption peak of light with a wavelength of 630 nm can be obtained, so that the photoelectric detector unit 1131 obtains the maximum receiving efficiency, thereby improving the accuracy of detection. For example, the photoelectric detector unit 1131 can also select light-emitter elements that emit light with a wavelength of 660 nm to detect the content of calcium and the content of protein in the liquid to be detected, and the maximum absorption peak of light with the wavelength of 660 nm can be obtained, so that the photoelectric detector unit 1131 obtains the maximum receiving efficiency, thereby improving the accuracy of detection. The photoelectric detector unit 1131 can also select light-emitter elements that emit light with a wavelength of 585 nm to detect the content of zinc in the liquid to be detected, and a maximum absorption peak of light with the wavelength of 585 nm can be obtained, so that the photoelectric detector unit 1131 obtains the maximum receiving efficiency, thereby improving the accuracy of detection. Therefore, the photoelectric sensor device 1133 of the photoelectric detector unit 1131 of the analyzer provided by the embodiments of the present disclosure can generate at least 5 detection signals (for example, corresponding to lactose, fat, zinc, calcium, and protein, respectively).

For example, in other embodiments, according to different reagents used in the detection areas of the detection chip 1200, different wavelengths of light can be selected to detect various substances in the liquid to be detected. For example, in some examples, the lower portion of the analyzer 1100 further includes an optical path component, the optical path component is arranged in the first shell 1110 between the chip placement structure 1120 and the detector unit, and is configured to transmit the light emitted by at least one light-emitter element 1132 to the chip placement structure 1120, and to transmit the light reflected from the detection chip 1200 placed on the chip placement structure 1120 to at least one photoelectric sensor device 1133. The optical path component can avoid the interference of light signals between different photoelectric detector units 1131, so that the reliability of the detection results is ensured.

For example, in some examples, as shown in FIG. 4A and FIG. 6A, the optical path component includes a light splitter disk 1141, which is arranged on the detector unit. The light splitter disk 1141 includes at least one group of light through holes 1142, the at least one group of light through holes 1142 are evenly arranged on the same circumference of the light splitter disk 1141, and correspond to a plurality of photoelectric detector units 1131 in a direction along an axis of the first shell 1110 respectively.

For example, in the present example, as shown in FIG. 6A, for example, the number of groups of light through holes 1142 is six. For another example, the number of groups of the light through holes 1142 may also be two, three, four, five, seven, etc., which corresponds to the number of the photoelectric detector units 1131. The embodiments of the present disclosure are not limited to the number of groups of the light through holes 1142.

For example, in some examples, each group of light through holes 1142 includes at least one light-emitting through hole and at least one light-reflecting through hole, the at least one light-emitting through hole allows the light emitted by the light-emitter element 1132 of the corresponding photoelectric detector unit 1131 to pass through, the at least one light-reflecting through hole allows the light reflected from the detection chip 1200 placed on the chip placement structure 1120 to pass through so as to transmit to the photoelectric sensor device 1133 of the corresponding photoelectric detector unit 1131. As shown in FIG. 6A, each group of light through holes 1142 includes two light-emitting through holes 1143 and one light-reflecting through hole 1144. The two light-emitting through holes 1143 are located at both sides of the light-reflecting through hole 1144, the light-emitting through holes 1143 correspond to the light-emitter elements 1132 in the photoelectric detector unit 1131, and the light-reflecting through hole 1144 corresponds to the photoelectric sensor device 1133 in the photoelectric detector unit 1131. The light emitted by the light-emitter elements 1132 passes through the light-emitting through holes 1143 and then is incident on the chip placement structure 1120, the light reflected from the detection chip 1200 placed on the chip placement structure 1120 passes through the light-reflecting through hole 1144 and then is received by the photoelectric sensor device 1133. The arrangement of the light splitter disk 1141 can avoid the interference of light signals between different photoelectric detector units 1131, so that the reliability of the detection results is ensured.

Figure 6B:
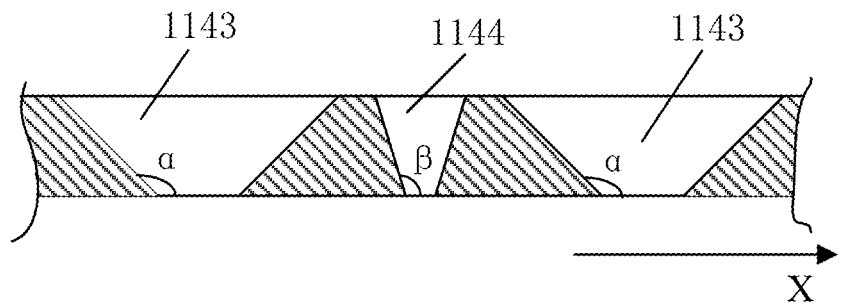
FIG. 6B is a cross-sectional schematic diagram of a group of light through holes of a light splitter disk provided by at least one embodiment of the present disclosure along the section line E-F in FIG. 6A.

For example, in some examples, as shown in FIG. 6B, the side wall of each of the light-emitting through holes 1143 of each group of light through holes 1142 is an inclined surface, the opening of each of the light-emitting through holes 1143 on the side facing away from the photoelectric detector units 1131 is larger than the opening of each the light-emitting through holes 1143 at the side close to the photoelectric detector units 1131, so that the irradiation area of the light emitted by the light-emitter elements 1132 on the detection chip 1200 can be increased. An angle between the side wall of each of the light-emitting through holes 1143 and an X direction (perpendicular to the axial direction of the light splitter disk 1141) is a. The value range of the included angle α is, for example, from about 130 degrees to about 140 degrees, for another example, the value of the included angle α is about 135 degrees, so that the incident light passing through the light-emitting through holes 1143 is emitted along the inclined surface of the long side of the light-emitting through holes 1143, the light can be better concentrated in the detection areas of the detection chip 1200, and a divergence of the incident light is reduced.

For example, the side wall of the light-reflecting through hole 1144 of each group of light through holes 1142 is an inclined surface, the opening of the light-reflecting through hole 1144 on the side facing away from the photoelectric detector units 1131 is larger than the opening of the light-reflecting through hole 1144 at the side close to the photoelectric detector units 1131, so that the interference between the light emitted by the light-emitter elements 1132 and the light reflected from the detection chip 1200 placed on the chip placement structure 1120 can be avoided. The angle between the side wall of the light-reflecting through hole 1144 and the X direction (perpendicular to the axial direction of the light splitter disk 1141) is β. The value range of the included angle β is, for example, from about 115 degrees to 125 degrees, for another example, the value of the included angle β is about 120 degrees. It should be noted that, the word "about" means that the value can be varied within, for example, ±15% of the value.

For example, in some examples, the light-emitting through holes 1143 include, for example, rectangular holes as shown in FIG. 6A. The size range of the opening of each of the light-emitting through holes 1143 at the side close to the photoelectric detector units 1131 in a circumferential direction and a radial direction is, for example, from about 0.8 mm to 1 mm. For another example, the size of each of the light-emitting through holes 1143 in both the circumferential direction and the radial direction is, for example, about 0.8 mm. The light-reflecting through hole 1144 include, for example, a circular hole as shown in FIG. 6A, and the value range of the diameter of the light-reflecting through hole 1144 is, for example, from about 0.8 mm to about 1 mm. For another example, the size of the opening of the light-reflecting through hole 1144 at the side close to the photoelectric detector unit 1131 in the circumferential direction, for example, is about 0.8 mm. It should be noted that, the word "about" means that the value can be varied within, for example, ±15% of the value. For another example, both the size of the light-emitting through holes 1143 and a diameter of the light reflecting through hole 1144 can be selected to be slightly larger than 1 mm according to the requirements of processing, so long as there is no optical crosstalk between two adjacent group of light through holes 1142. The embodiments of the present disclosure is not limited by the specific size of the light-emitting through holes 1143 and the light reflecting through hole 1144.

For example, in some examples, as shown in FIG. 6A, the value range of a long side of the light-emitting through hole 1143 is, for example, from about 3.5 mm to about 4.5 mm, for another example, the value of the long side of the light-emitting through hole 1143 is about 4 mm. The value range of a short side of the light-emitting through hole 1143 is, for example, from about 3 mm to about 3.4 mm, for another example, the value of the short side of the light-emitting through hole 1143 is about 3.2 mm. It should be noted that, the word "about" means that the value can be varied within, for example, ±15% of the value. The light-emitting through holes 1143 include rectangular holes, so that the incident light passing through the light-emitting through holes 1143 is emitted along the inclined surfaces of the long side of the light-emitting through hole 1143, the light can be better concentrated in the detection areas of the detection chip 1200, and the divergence of the incident light is reduced.

Figure 6C:
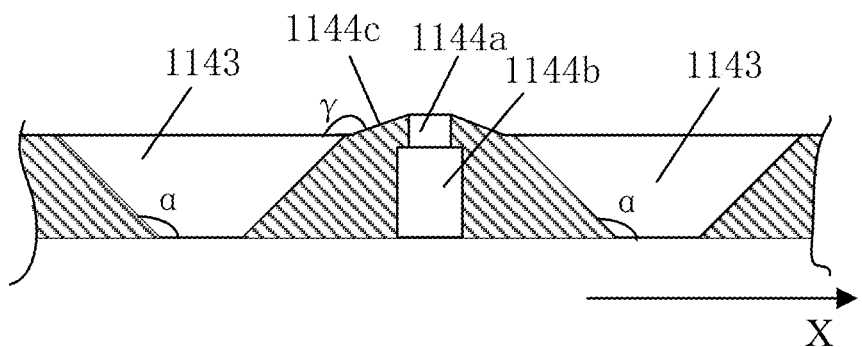
FIG. 6C is another cross-sectional schematic diagram of a group of light through holes of a light splitter disk provided by at least one embodiment of the present disclosure along the section line E-F in FIG. 6A.

FIG. 6C is another cross-sectional schematic diagram of a group of light through holes of a light splitter disk provided by at least one embodiment of the present disclosure along the section line E-F in FIG. 6A. As shown in FIG. 6C, the light-reflecting through hole 1144 includes a first reflecting through sub-hole 1144b close to the first side of the light splitter disk 1141 (a lower side in the figure, that is, the side where the incident light enters), and a second reflecting through sub-hole 1144a close to the second side of the light splitter disk 1141 (the upper side in the figure, that is, the side where the reflected light is reflected). For example, the diameter of the first reflecting through sub-hole 1144b is smaller than the diameter of the second reflecting through sub-hole 1144a, so that the light emitted from the light-emitting through holes 1143 can be shielded from entering the light-emitting through holes, and causing detection errors is avoided.

For example, the size range of the diameter of the first reflecting through sub-hole 1144b is, for example, from about 0.8 mm to about 1.2 mm. For another example, the size of the diameter of the first reflecting through sub-hole 1144b is, for example, about 1 mm. For example, the size range of the diameter of the second reflecting through sub-hole 1144a is, for example, from about 1.4 mm to about 1.8 mm. For another example, the size of the diameter of the second reflecting through sub-hole 1144a is, for example, about 1.6 mm. It should be noted that, the word "about" means that the value can be varied within, for example, ±15% of the value. Thus, the light emitted from the light-emitting through holes 1143 can be shielded from entering the light-emitting through holes, and causing detection errors is avoided, under this case, the reflected light entering the first reflecting through sub-hole 1144b is not reflected.

For another example, as shown in FIG. 6C, an upper surface (for example, the surface close to the second side) of the light splitter disk 1141 includes at least one protrusion 1144c. The protrusion 1144c protrudes obliquely from the side of the two light-emitting through holes 1143 close to the light-reflecting through hole 1144 to the second side in the direction close to the light-reflecting through hole 1144. The first reflecting through sub-hole 1144b is located in the protrusion 1144c, so that the light emitted from the light-emitting through holes 1143 can be shielded from entering the light-emitting through holes, and causing detection errors is avoided.

For another example, as shown in FIG. 6C, the protrusion 1144c is in an annular shape, the protrusion 1144c surrounds the first reflecting through sub-hole 1144b. The light emitted from the light-emitting through holes 1143 can be shielded from entering the light-emitting through holes, and causing detection errors is avoided.

For example, as shown in FIG. 6C, the value range of the slope angle α of the protrusion 1144c is, for example, from about 130° to about 140°, for another example, the value of the slope angle α of the protrusion 1144c is, for example, about 135°. For example, the value range of the height of the protrusion 1144c protruding from the light-emitting through holes 1143 is, for example, from about 0.4 mm to about 0.6 mm, for another example, the height of the protrusion 1144c protruding from the light-emitting through holes 1143 is, for example, about 0.5 mm. For example, it should be noted that the word "about" means that the value can vary within, for example, ±15% of the value. Therefore, the inclined surface provided by the protrusion 1144c can shield the light emitted from the light-emitting through holes 1143 for the first reflecting through sub-hole 1144b.

For example, in other examples, the shapes of the light-emitting through holes 1143 can also include a triangle shape, a circle shape, and a polygonal shape, etc., the shape of the light-reflecting through hole 1144 can also include a rectangle shape, a triangle shape, and a polygonal shape, etc., and the embodiments of the present disclosure is not limited by the shapes of the light-emitting through holes 1143 and the shape of the light-reflecting through hole 1144.

For example, in some examples, the light splitter disk 1141 further includes at least one second positioning hole. As shown in FIG. 6A, the light splitter disk 1141 includes three second positioning holes 1145, which are evenly distributed on a same circumference. The number of the second positioning holes 1145 may also be two, four, etc., which is not limited in the embodiments of the present disclosure. As shown in FIG. 4A, first positioning holes 1303 of the detection circuit board 1302 are provided at a positions of the detection circuit board 1302 opposite to the second positioning holes 1145 of the light splitter disk 1141. The first positioning holes 1303 of the detection circuit board 1302 and the second positioning holes 1145 are configured to install and position of both the light splitter disk 1141 and the detection circuit board 1302, so that the photoelectric detector units 1131 corresponds to the light through holes 1142.

For example, in some examples, as shown in FIG. 3 and FIG. 6A, the light splitter disk 1141 further includes a limiter block 1146, and the limiter block 1146 is arranged at the edge of the light splitter disk 1141. The limiter block 1146 extends into the chip placement structure 1120 to match the shape of the detection chip 1200. In the case where the detection chip 1200 is placed in the chip placement structure 1120, the position of the detection chip 1200 is fixed, so that the plurality of detection areas of the detection chip 1200 correspond to the light through holes 1142 of the light splitter disk 1141 and the photoelectric detector units 1131 respectively.

For example, in other examples, the limiter block 1146 may also be arranged on other structures of the analyzer 1100, such as the first shielding plate 1301. For another example, the limiter block 1146 can also be replaced with other structures that can achieve alignment with the detection chip 1200, which is not limited in the embodiments of the present disclosure.

For example, in other embodiments, the limiter block 1146 can also be replaced by a positioning pin or a positioning hole, and a corresponding matching structure is arranged on the detection chip 1200.

For example, in some examples, as shown in FIG. 4A, the lower portion of the analyzer 1100 further includes a separator component 1150, such as, a partition plate, which is located in the first shell 1110 and is arranged between the optical path component and the chip placement structure 1120. That is, the separator component 1150 is located above the optical path component and below the chip placement structure 1120. The separator component 1150 includes a light-transmitter portion 1151, which is configured to allow the light emitted by the light-emitter elements 1132 of the photoelectric detector units 1131 and the light reflected from the detection chip 1200 placed on the chip placement structure 1120 to pass through. The detection chip 1120 is located above the separator component 1150, and the separator component 1150 is configured to prevent the penetration of the liquid to be detected in the detection areas of the detection chip 1120. For example, the separator component 1150 can also provide protection functions for the optical path components arranged below. In other examples, the separator component 1150 arranged at the lower portion of the analyzer 1100 can be disassembled for easy replacement.

For example, in some examples, as shown in FIG. 4A, the light-transmitter portion 1151 of the separator component 1150 includes at least one transparent window 1152, which respectively corresponds to the plurality of photoelectric detector units 1131, and respectively allows the light emitted from the at least one light-emitter element 1132 of the corresponding photoelectric detector unit 1131 and the light reflected from the detection chip 1200 placed on the chip placement structure 1120 to the at least one photoelectric sensor device 1133 of the corresponding photoelectric detector unit 1131 to pass through.

For example, in the example, as shown in FIG. 4A, the number of the group of the transparent windows 1152 is, for example, six. For another example, the number of the group of the transparent windows 1152 can also be two, three, four, five, seven, etc., which corresponds to the number of the group of the light through holes 1142. The embodiments of the present disclosure is not limited by the number of the group of the transparent windows 1152.

Figure 4B:
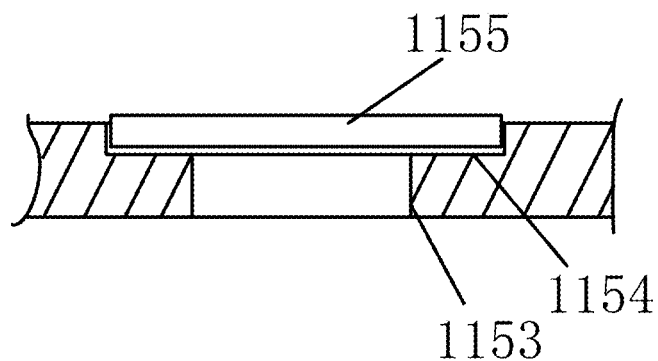
FIG. 4B is a cross-sectional schematic diagram of a transparent window of a separator component provided by at least one embodiment of the present disclosure.

For example, in some examples, as shown in FIG. 4A and FIG. 4B, each of the transparent windows 1152 includes a first through hole 1153, a first groove 1154, and a transparent sheet 1155. The diameter of the first through hole 1153 is smaller than the diameter of the first groove 1154, the first groove 1154 is located at a side of the separator component 1150 close to the chip placement structure 1120, and the first groove 1154 is configured to place the transparent sheet 1155. The transparent sheet 1155 is placed in the first groove 1154, which allows the light emitted by the two light-emitter elements 1132 of the corresponding photoelectric detector unit 1131 and the light reflected from the detection chip 1200 placed on the chip placement structure 1120 to the photo- electric sensor device 1133 of the corresponding photoelectric detector unit 1131 to pass through.

For example, the value range of the diameter of the transparent sheet 1155 is, for example, from about 5.5 mm to about 7 mm, for another example, the value of the diameter of the transparent sheet 1155 is, for example, about 6.3 mm. For example, the value range of the thickness of the transparent sheet 1155 is, for example, from about 0.3 mm to about 0.7 mm, for another example, the thickness of the transparent sheet 1155 is, for example, about 0.5 mm. The smaller the thickness of the transparent sheet 1155, the better the light transmission, which is not limited in the present disclosure. For example, the value range of the diameter of the first through hole 1153 is, for example, from about 3 mm to about 3.8 mm, for another example, the value of the diameter of the first through hole 1153 is, for example, about 3.4 mm. It should be noted that, the word "about" means that the value can be varied within, for example, ±15% of the value. Therefore, the value of the diameter of the first through hole 1153 can allow the light incident from the light-emitting through holes 1143 on both sides of the light-reflecting through hole 1144 better converge in the detection areas of the detection chip 1200, so that the divergence of incident light is reduced, and the detection accuracy is improved.

For example, in some examples, the transparent sheet 1155 may include a glass sheet or a transparent acrylic sheet, etc.

For example, in other examples, the light-transmitter portion 1151 may also be other light-transmitting structures, for example, a structure formed by a light-transmitting hole and the transparent sheet 1155, or a structure formed by removing the transparent sheet 1155 in the transparent window 1152. The embodiments of the present disclosure are not limited by the specific structure of the light-transmitter portion 1151.

For example, in other examples, the separator component 1150 may also be an overall transparent structure without arranging the transparent window 1152. For example, the separator component 1150 is made of transparent material, so that the separator component 1150 may allow the light emitted by the light-emitter elements 1132 of the photoelectric detector unit 1131 and the light reflected from the detection chip 1200 placed on the chip placement structure 1120 to the photoelectric sensor device 1133 of the corresponding photoelectric detector unit 1131 to pass through, and leakage of the liquid to be detected in the detection chip 1200 is prevent. The embodiments of the present disclosure are not limited to this.

In some other examples, the separator component 1150 may not be included, transparent windows are provided on the light through holes of the light splitter disk 1141, under this case, the light splitter disk 1141 can also prevent the penetration of the liquid to be detected in the detection areas of the detection chip 1120.

For example, in some examples, as shown in FIG. 4A, the separator component 1150 further includes a plurality of positioning columns 1156, which are arranged on a side of the separator component 1150 close to the light splitter disk 1141. For another example, the separator component 1150 includes three positioning columns 1156, the three positioning columns 1156 correspond to the positioning holes 1145 of the light splitter disk 1141 and the positioning holes 1303 of the detection circuit board 1302. In addition, the positioning columns 1156 of the separator component 1150 are installed in the positioning holes 1145 of the light splitter disk 1141 and the positioning holes 1303 of the detection circuit board 1302, so that the separator component 1150, the light splitter disk 1141 and the detection circuit board 1302 are fixed, and the light-transmitter portion 1151 of the separator component 1150, the light through hole 1142 of the light splitter disk 1141, and the photoelectric detector unit 1131 correspond with each other in an axial direction of the first shell 1110.

For example, in other examples, the second positioning holes 1145 are arranged at the separator component 1150, the positioning columns 1156 are arranged at the light splitter disk 1141, the positioning columns 1156 extend to the upper side and the lower side of the light splitter disk 1141, the positioning columns 1156 can also be installed in the positioning holes 1145 of the light splitter disk 1141 and the positioning holes 1303 of the detection circuit board 1302, so that the separator component 1150, the light splitter disk 1141, and the detection circuit board 1302 are fixed. The embodiments of the present disclosure is not limited by the installation method of the separator component 1150, the light splitter disk 1141, and the detection circuit board 1302.

For example, in other examples, other methods can also be used to fix the separator component 1150, the light splitter disk 1141, and the detection circuit board 1302, for example, using double-sided adhesive tape, or using lockers, etc.

Figure 7:
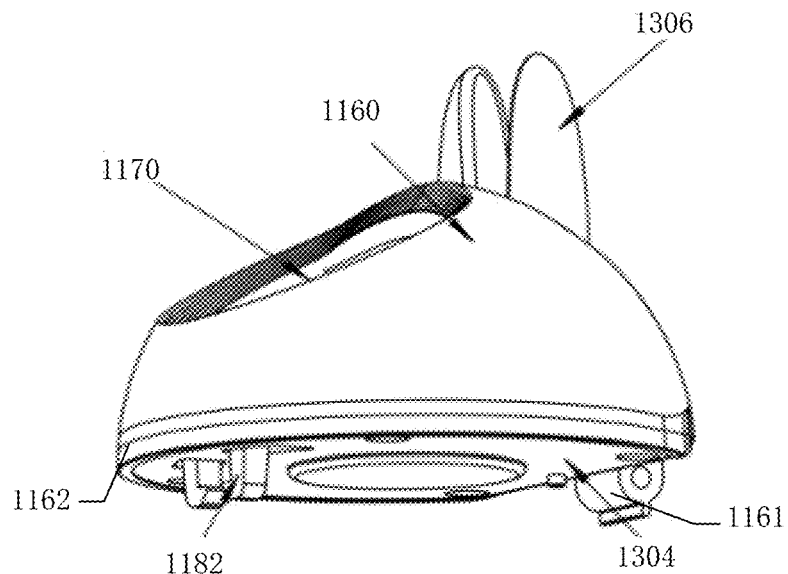
FIG. 7 is a schematic diagram of a second shell of the analyzer provided by at least one embodiment of the present disclosure.

For example, in some examples, as shown in FIG. 7, the analyzer 1100 further includes a second shell 1160, and the second shell 1160 is connected to the first shell 1110. The chip placement structure 1120 and the detector unit are arranged in a space enclosed by the first shell 1110 and the second shell 1160. For example, in the present embodiment, the detector unit as shown in FIG. 2 and FIG. 3 is arranged on the detection circuit board 1302 and are located in the first shell 1110. The first shell 1110 and the second shell 1160 are connected with each other at a first side 1161, and the first shell 1110 and the second shell 1160 can be relatively closed and opened at a second side 1162, so that the detection chip 1200 is placed on the chip placement structure 1120, or the detection chip 1200 is taken out from the chip placement structure 1120. It should be noted that, in the example as shown in the figure, the first side 1161 is a side that the first shell 1110 and the second shell 1160 are connected with each other, the second side 1162 is a side that the first shell 1110 and the second shell 1160 are relatively opened and closed, that is, the side that the detection chip 1200 is placed, the first side 1161 is arranged opposite to the second side 1162, and the relative positions of the first side 1161 and the second side 1162 do not constitute a limitation to the embodiments of the present disclosure. The first shell 1110 is approximately in a hemispherical shape, and the shape of the opening below the first shell 1110 is the same as the shape of the opening above the second shell 1160, so that a closed space that outside ambient light cannot be entered is formed in the case where the first shell 1110 and the second shell 1160 are closed to facilitate the detection of the analyzer 1100.

For example, in other examples, the shape of the second shell 1160 may also be, for example, a cuboid, an opening shape of the second shell 1160 and an opening shape of the first shell 1110 are matched with each other, as long as the closed space can be formed, which is not limited in the embodiments of the present disclosure.

For example, in some examples, as shown in FIG. 2 and FIG. 7, the second shell 1160 and the first shell 1110 are hinged. The second shell 1160 is configured to be closed with the first shell 1110 at the second side 1162, and to be opened to expose the chip placement structure 1120. The first side 1161 and the second side 1162 are arranged opposite to each other.

For example, in some examples, as shown in FIG. 2, the first shell 1110 and the second shell 1110 are hinged at the first side 1161 by a hinge shaft 1163. A spring (such as a torsion spring) can also be arranged at the hinge shaft 1163, so that after the first shell 1110 and the second shell 1160 are opened at the second side, the second shell 1160 will tilt up under the elastic force of the spring.

Figure 8:
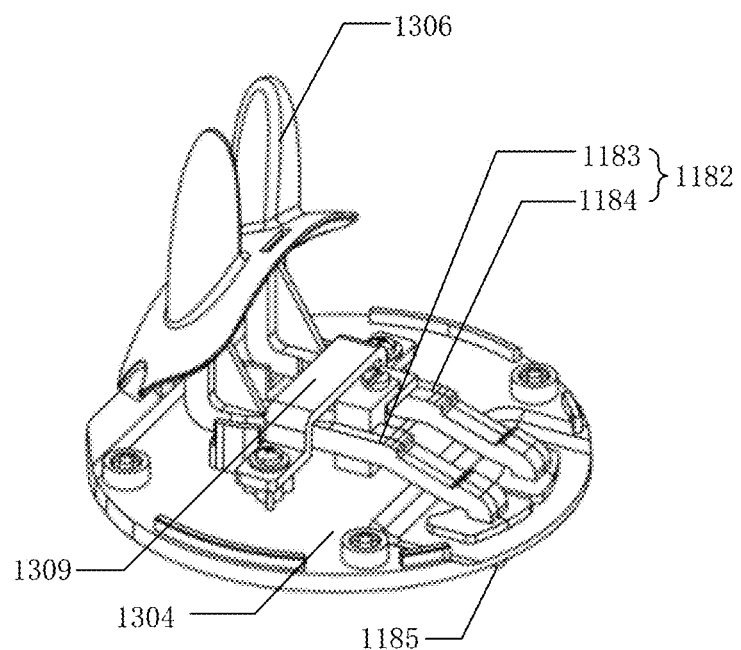
FIG. 8 is a structural schematic diagram of a second shell of the analyzer provided by at least one embodiment of the present disclosure.

For example, in some examples, as shown in FIG. 8, the second shell 1160 further includes a second shielding plate 1304 that connected with the lower side of the second shell 1160, for example, a snap connection, and a screw connection and so on. The second shielding plate 1304 and the first shielding plate 1301 in the first shell 1110 form an accommodating space together for the detection chip. The second shielding plate 1304 can shield other stray light in the second shell 1160 to avoid interference of other light on the detection result.

For example, in some examples, as shown in FIG. 3 and FIG. 8, the first shell 1110 includes a first opening and closing sub-component 1181 arranged at the second side 1162, the second shell 1160 includes a second opening and closing sub-component 1182 arranged at the second side 1162. The first opening and closing sub-component 1181 and the second opening and closing sub-component 1182 are configured to be combined with each other and separated from each other, so that the first shell 1110 and the second shell 1160 can be closed and opened with each other, respectively. In the case where the first shell 1110 and the second shell 1160 are opened, the detection chip 1200 is placed on the chip placement structure 1120, after that, the first shell 1110 and the second shell 1160 are closed, and then the substance detection is started.

Figure 9:
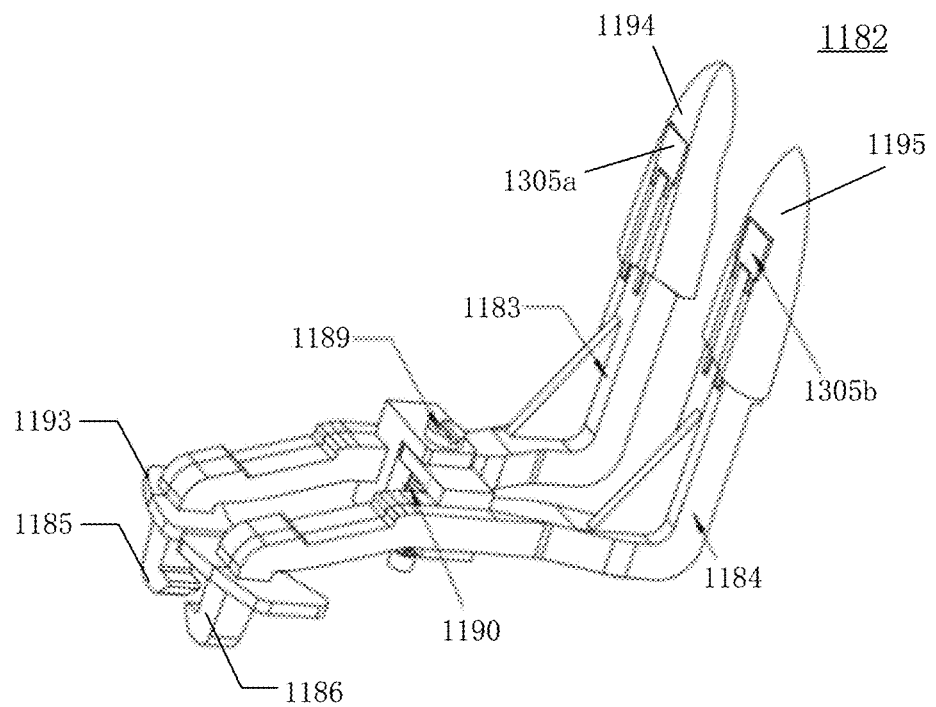
FIG. 9 is a schematic diagram of a second opening and closing sub-component of an opening and closing component of the analyzer provided by at least one embodiment of the present disclosure.

As shown in FIG. 3, FIG. 8 and FIG. 9, the second opening and closing sub-component 1182 includes a first locking tongue 1183 with a long strip shape and a second locking tongue 1184 with a long strip shape, the first locking tongue 1183 and the second locking tongue 1184 are paired and arranged substantially side by side in the second shell 1160. The first locking tongue 1183 and the second locking tongue 1184 may be fixed on the second shielding plate 1304. The fixing method is, for example, a screw connection. A first end portion 1185 of the first locking tongue 1183 and a first end portion 1186 of the second locking tongue 1184 are exposed from the second shielding plate 1304. The first opening and closing sub-component 1181 includes a groove 1187 and a locker 1188, and the locker 1188 is located in the groove 1187. The first end portion 1185 of the first locking tongue 1183 and the first end portion 1186 of the second locking tongue 1184 are configured to extend into the groove 1187 and be snapped with the locker 1188, so that the first shell 1110 and the second shell 1160 can be closed and can be detached from the locker, thus the first shell 1110 and the second shell 1160 are opened.

For example, in some examples, as shown in FIG. 8, the analyzer 1100 further includes a fixing component 1309, a middle portion of the first locking tongue 1183 and a middle portion of the second locking tongue 1184 are fixed at the second shielding plate 1304 by the fixing component 1309.

For example, in some examples, the second opening and closing sub-component 1182 further includes an elastic component, the elastic component is arranged in both the middle portion of the first locking tongue 1183 and the middle portion of the second locking tongue 1184 to elastically connect the first locking tongue 1183 and the second locking tongue 1184, and the elastic component is configured to apply elastic force to tend to place the first tongue 1183 and the second tongue 1184 in a state that the first tongue 1183 and the second tongue 1184 can be snapped with the locker 1188.

For example, in some examples, as shown in FIG. 9, the elastic component includes a torsion spring 1190, and the torsion spring 1190 is configured to apply an elastic force to allow the first end portion 1185 of the first locking tongue 1183 and the first end portion 1186 of the second locking tongue 1184 approach each other, so that the first end portion 1185 of the first locking tongue 1183 and the first end portion 1186 of the second locking tongue 1184 are in a clamped state. A second end portion 1194 of the first locking tongue 1183 and a second end portion 1195 of the second locking tongue 1184 extend to the outside of the second shell 1160.

For example, in some examples, by reducing an opening distance between the second end portion 1194 of the first locking tongue 1183 and the second end portion 1195 of the second locking tongue 1184, the first end portion 1185 of the first locking tongue 1183 and the first end portion 1186 of the second locking tongue 1184 are separated from the locker 1188 in a state of being snapped with the locker 1188, so that the first shell 1110 and the second shell 1160 are opened.

For example, in some examples, the second opening and closing sub-component 1182 further includes switches, the switches are arranged in the middle portion of the first locking tongue 1183 and the middle portion of the second locking tongue 1184, and the switches are connected with both the first locking tongue 1183 and the second locking tongue 1184, respectively. In addition, the switches are configured to be operable, so that the first end portion 1185 of the first locking tongue 1183 and the first end portion 1186 of the second locking tongue 1184 are separated from the locker 1188 in a state of being snapped with the locker 1188.

For example, in some examples, as shown in FIG. 9, the second opening and closing sub-component 1182 further includes a micro switch 1305a and a micro-switch 1305b the micro-switch 1305a is arranged at the second end portion 1194 of the first locking tongue 1183, and the micro-switch 1305b is arranged at the second end portion 1195 of the second locking tongue 1184. One of the micro-switch 1305a and the micro-switch 1305b is configured to realize the switch function of the analyzer 1100, the other one of the micro-switch 1305a and the micro-switch 1305b is configured to realize the function of the analyzer 1100 to control the display of the detection results. For example, long time pressing the micro-switch 1305a will turn on the analyzer 1100, and start the detection of the detection chip 1200. Short time pressing the micro-switch 1305a will turn off the analyzer 1100; and pressing the micro-switch 1305b will select the detection results to be displayed.

For example, in some examples, as shown in FIG. 9, the second opening and closing sub-component 1182 further includes a rotating shaft 1189, the middle portion of the first locking tongue 1183 and the middle portion of the second locking tongue 1184 are connected with each other, and the torsion spring 1190 is sleeved on the rotating shaft 1189.

Figure 10:
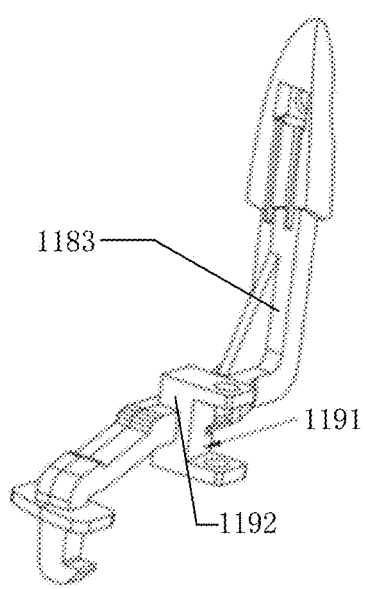
FIG. 10 is a schematic diagram of a partial structure of a second opening and closing sub-component of the analyzer provided by at least one embodiment of the present disclosure.

For example, in some examples, as shown in FIG. 10, a connector component 1192 is arranged in the middle portion of the first locking tongue 1183 of the second opening and closing sub-component 1182, the surface of the connector component 1192 opposite to the second locking tongue 1184 is an inclined surface, to form a limiter track 1191. The limiter track 1191 is configured to limit the opening and closing angles of the first locking tongue 1183 and the second locking tongue 1184 to prevent the opening distance between the first end portion 1185 of the first locking tongue 1183 and the first end portion 1186 of the second locking tongue 1184 from being too small, and to prevent the second end portion 1194 of the first locking tongue 1183 and the second end portion 1195 of the second locking tongue 1184 from being too large, which will cause the opening angle of the second shell 1160 relative to the first shell 1110 to be too large. For example, the angle between the second shell 1160 and the first shell 1110 is greater than 90 degrees, so that the second shell 1160 rolls over in a direction away from the second side 1162, and the analyzer 1100 is at risk of dumping.

For example, in some examples, as shown in FIG. 7, the analyzer 1100 further includes a displayer device 1170, which is arranged at the second shell 1160. The displayer device 1170 may be, for example, a liquid crystal displayer device, an organic light-emitting diode (OLED) displayer device, an electronic paper, or a digital tube, which is used for displaying the detection results of the analyzer 1100.

For example, in some examples, as shown in FIG. 7, FIG. 8, and FIG. 9, the analyzer 1100 further includes a silicone sleeve 1306, which is sleeved on the second end portion 1194 of the first locking tongue 1183 and the second end portion 1195 of the second locking tongue 1184, to achieve the effects of being beautiful, being dustproof, and preventing light from entering the second shell 1160.

For example, in some examples, as shown in FIG. 9, light shielding components 1193 are arranged on the first end portion 1185 of the first locking tongue 1183 and the first end portion 1186 of the second locking tongue 1184 respectively, to shield the light in the second shell 1160.

For example, in some examples, as shown in FIG. 5A, the analyzer 1100 further includes a controller device 1310, which is connected in signal with the photoelectric detector units 1131 and the displayer device 1170. The controller device 1310 is configured to receive detection results of the photoelectric detector units 1131 and send the detection results to the displayer device 1170, and the displayer device 1170 can display the received detection results. For example, the controller device can include a processor and a memory, the processor can include a central processor unit (CPU) or a data processor (DSP), and the memory may include a semiconductor memory, which is configured to store computer codes for execution on the processor and for storing data. The controller device 1310 is also connected with the micro-switch 1305a and the micro-switch 1305b to perform a switching function of the analyzer 1100 and a function of controlling the display of the detection results on the displayer device 1170. For example, long time pressing the micro-switch 1305a will turn on the analyzer 1100 and start the detection of the detection chip 1200, short time pressing the micro-switch 1305a will turn off the analyzer; the display contents of the displayer device 1170 is controlled by pressing the micro-switch 1305b, and the detection results can be viewed on the displayer device 1170 according to the selection.

For example, in some examples, as shown in FIG. 5A, the analyzer 1100 further includes a sound generator device 1311, and a signal transmitter and receiver device 1312, etc. The sound generator device 1311 includes, for example, a speaker, which generates reminding sounds as requirements. The signal transmitter and receiver device 1312 includes, for example, an antenna, a modem, etc., which is configured to communication, for example, using bluetooth, WIFI, mobile communication (such as 2G/3G/4G/5G, etc.) to communicate, so that the detection results can be sent to other devices (for example, mobile terminals such as mobile phones, tablets, etc., or servers, etc.), for example, the detection results are uploaded to applications (APP) installed on mobile terminals such as mobile phones in real time. Or control signals received from other devices are used to control the operation of the analyzer by the controller device, for example, it is possible to cooperate with the analyzer 1100 by installing an application program (APP) on mobile terminals such as mobile phones. For example, in some examples, the analyzer 1100 further includes a temperature sensor, which is configured to monitor the ambient temperature of the analyzer 1100. because some liquid to be detected have certain requirements for the temperature during detection, for example, the temperature needs to be approximately in the range of 25° C. to 35° C. Therefore, detecting the ambient temperature of the analyzer 1100 can ensure the accuracy of the detection results.

For example, in some examples, the analyzer 1100 may also include a humidity sensor, which is configured to detect the environmental humidity of the analyzer 1100. In the process of detecting, some liquid to be detected have certain requirements for the humidity during detecting, for example, a color reaction occurs between the liquid to be detected and the test paper in the detection areas of the chip, in response to lower the humidity, the test paper may fade and affect the detect results. The control of the environmental humidity during the detection process helps to ensure the accuracy of the detection results.

For example, in some examples, as shown in FIG. 3, the analyzer 1100 further includes a battery 1307, which is arranged in the first shell 1110. The battery 1307 supplies power to each device in the analyzer 1100 that needs to use electric energy, for example, supplying power to the controller device, the displayer device, and the detector unit. For example, the battery 1307 may include a primary battery or a secondary battery, and the secondary battery may include a nickel-hydrogen battery, a nickel-cadmium battery, a lead-acid battery, and a lithium-ion battery, etc. The analyzer 1100 provided by the embodiments of the present disclosure has a simple structure, and a low power consumption, so that the analyzer 1100 has a long standby time to facilitate the usage of users. For another example, the analyzer 1100 can also use a power cable to provide electrical energy for various devices that need to use electrical energy. According to the requirements of the analyzer 1100 in usage, battery power supply or direct power supply can be selected.

For example, in some examples, as shown in FIG. 3, the analyzer 1100 further includes a counterweight 1308, which is arranged in the first shell 1110 and is located under the battery 1307. The counterweight 1308 is configured to move the center of gravity of the analyzer 1100 down, so that the analyzer 1100 is more stable as placed on a horizontal surface, and the detection chip 1200 can be made not easy to move in the case where the detection chip 1200 is placed on the chip placement structure 1120, thereby ensuring the reliability of the detection results.

In addition, in at least one embodiment, the analyzer may have the characteristics of small size, simple structure, and easy operation, is suitable for use at home, and can monitor the content of various substances in liquid such as breast milk at any time.

Figure 11:
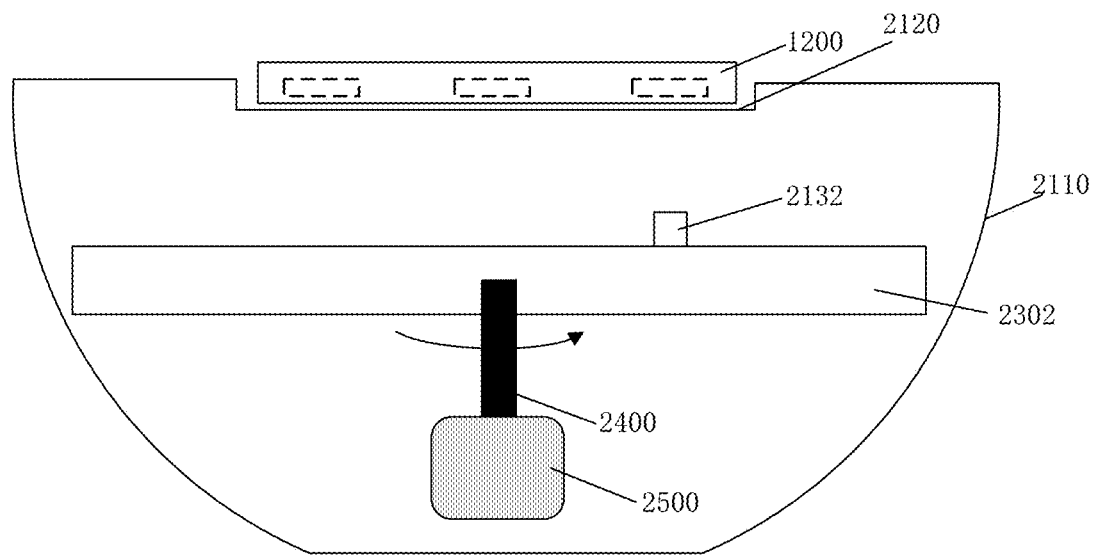
FIG. 11 is another schematic diagram of a partial structure of the analyzer provided by at least one embodiment of the present disclosure.

Another embodiment of the present disclosure also provides an analyzer, as shown in FIG. 11, the analyzer includes a first shell 2110, a chip placement structure 2120, and a detector unit. The chip placement structure 2120 is arranged in the first shell 2110, and is configure to place the detection chip 1200. The detection chip 1200 includes at least one detection area. The detector unit is rotatably arranged in the first shell with respect to the chip placement structure 2120, which includes, for example, a photoelectric detector unit, and the photoelectric detector unit includes, for example, at least one photoelectric detector unit 2132, such as a single photoelectric detector unit. The photoelectric detector unit 2132 is configured to that in the case where the detection chip 1200 is placed on the chip placement structure 2120, the plurality of detection areas of the detection chip 1200 can be respectively detected by relative rotation with the detection chip 1200, for example, the detection chip 1200 can be rotated or the photoelectric detector unit can be rotated to detect the plurality of detection areas of the detection chip 1200 respectively. For example, the photoelectric detector unit 2132 includes at least one light-emitter element and at least one photoelectric sensor device, or for example, only includes a photoelectric sensor device.

In an example, the photoelectric detector unit 2132 of the analyzer is rotatably arranged in the first shell 2110 with respect to the chip placement structure 2120, the analyzer can respectively detect the plurality of detection areas of the detection chip by a photoelectric detector unit of the detector unit, so that the content of various substances in the liquid to be detected in the detection chip is detected. In the example, the same light-emitter element included in the photoelectric detector unit 2132 can emit light of different wavelengths as required, to perform corresponding detections on different detection samples.

The structure difference between the analyzer provided in the embodiment and the previous embodiments is that: the detector unit in the embodiment is relatively rotatable with respect to the chip placement structure in the first shell, and the detector unit only includes at least one photoelectric detector unit. Hereinafter, the different portions of the structure of this embodiment and the previous embodiments will be introduced.

For example, in some examples, as shown in FIG. 11, the detector unit is arranged on the detection circuit board 2302. A central axis 2400 is arranged at the center of the detection circuit board 2302. The analyzer also includes a rotation driver device 2500, which is connected with the controller device, in this way, the rotation driver device 2500 is controlled by the controller device. The rotation driver device 2500, for example, may include a servo motor, or a stepping motor. The other end of the central axis 2400 is connected with the rotation driver device 2500, the rotation driver device 2500 drives the central axis 2400 to rotate so as to drive the photoelectric detector unit 2132 of the detector unit to rotate relative to the chip placement structure 2120.

For example, in some examples, at least one photoelectric detector unit includes one photoelectric detector unit, the rotation driver device is configured to drive a photoelectric detector unit to rotate with respect to the chip placement structure.

For example, in some examples, compared with the previous embodiments, the analyzer in the present embodiment can connect the light splitter disk of the optical path component and the separator component to the first shell, instead of connecting with the detection circuit board, which is ensured that the light through holes of the light splitter disk and the light-transmitter portion of the separator component correspond to the detection areas of the detection chip.

For another example, in some examples, compared with the previous embodiments, the analyzer of the present embodiment can change the light through holes of the light splitter disk of the optical path component and the light-transmitter portion of the partitioning component to one group, which corresponds to the detector unit. The light splitter disk and the separator component rotate together with the detection circuit board 2132, the detection chip 1200 is placed on the chip placement structure 2120, and the position of the detection chip 1200 does not move. For example, a limiting spring sheet can be arranged at the sidewall of the chip placement structure, and in the case where the detection chip 1200 is placed on the chip placement structure 2120, the position of the detection chip is fixed.

For example, in some examples, the rotation driver device 2500 receives signals from the controller device and controls a rotation angle of the photoelectric detector unit 2132, so that the photoelectric detector unit 2132 stops rotating in the case where the photoelectric detector unit 2132 rotates to a position corresponding to a detection area of the detection chip 1200, the photoelectric detector unit 2132 detects the substance content in the detection area. The controller device receives an electrical signal from the photoelectric sensor device of the photoelectric detector unit 2132, the photoelectric detector unit 2132 is rotated again to a position corresponding to another detection area of the detection chip 1200, and then the substance content in the detection area is started to detect. According to the above method, the analyzer can sequentially detect the substance content in the plurality of detection areas of the detection chip 1200, so that the contents of various substances in the liquid to be detected can be obtained.

At least one embodiment of the present disclosure provides a detection system, the detection system includes the analyzer and the detection chip described in any one of the above embodiments, for example, provided as a kit. The detection chip is configured to be placeable on the chip placement structure of the analyzer.

Figure 12A:
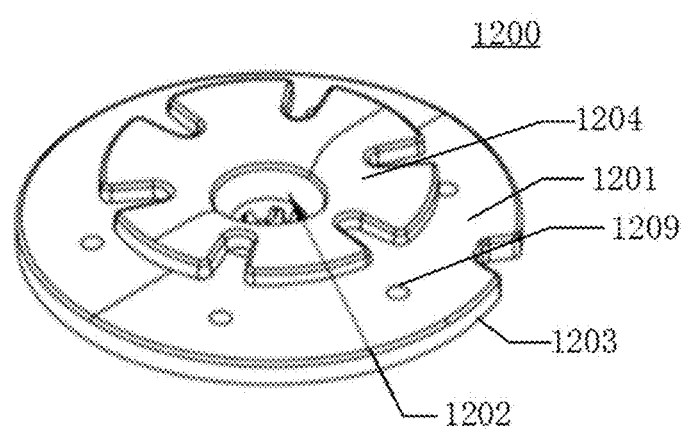
FIG. 12A is a schematic diagram of a detection chip provided by at least one embodiment of the present disclosure.
Figure 12B:
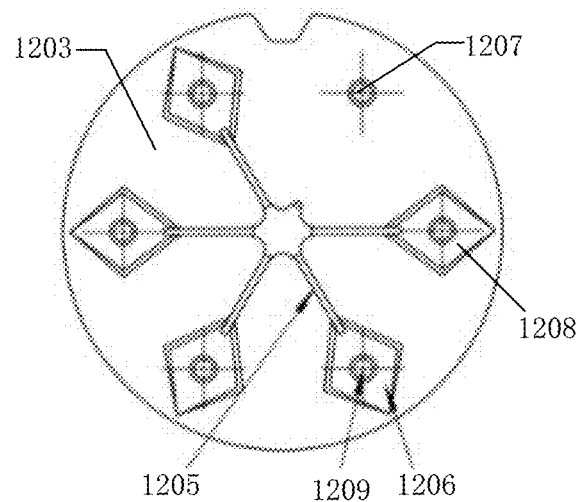
FIG. 12B is a schematic diagram of a partial structure of a detection chip provided by at least one embodiment of the present disclosure.
Figure 12C:
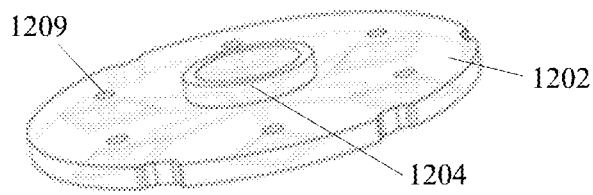
FIG. 12C is an exploded schematic diagram of another detection chip provided by at least one embodiment of the present disclosure.
Figure 12C:
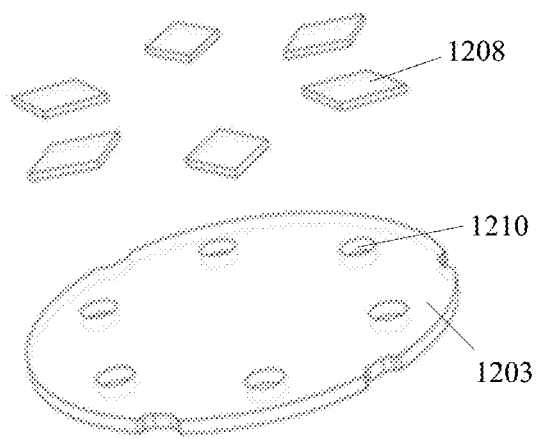

FIG. 12A is a schematic diagram of a detection chip provided by at least one embodiment of the present disclosure; FIG. 12B is a schematic diagram of a partial structure of a detection chip provided by at least one embodiment of the present disclosure; FIG. 12C is an exploded schematic diagram of another detection chip provided by at least one embodiment of the present disclosure.

As shown in FIG. 12A and FIG. 12B, the detection chip includes a cover plate 1201 and a substrate 1203. The cover plate 1201 includes a sample injection opening 1202 and the cover plate 1201 is closely attached to the substrate 1203. The substrate 1203 is made of a transparent material to allow the light emitted by the photoelectric detector units 1131 in the analyzer 1100 to enter the detection chip 1200 and the light reflected by the detection chip 1200 to be transmitted to the photoelectric detector units 1131.

For example, in some examples, as shown in FIG. 12B, a plurality of micro flow channels 1205, a plurality of detection areas 1206, and a calibration area 1207 are arranged on the surface of the cover plate 1201 opposite to the substrate 1203. The detection chip includes five detection areas 1206. Each of the detection areas 1206 is connected with one end of the plurality of micro flow channels 1205, the other end of plurality of micro flow channels 1205 extend to the sample injection opening 1202 of the cover plate 1201, so that the liquid to be detected enters the plurality of detection areas 1206 through the plurality of micro flow channels 1205. For example, the center of the calibration area 1207 and the centers of the plurality of detection areas 1206 are arranged on the same circumference at equal intervals, the plurality of detection areas 1206 and the calibration area 1207 respectively correspond to the photoelectric detector units 1131 in the detector unit of the analyzer 1100. The calibration area 1207 is configured to detect and systematically calibrate whether there is a detection chip 1200 on the chip placement structure 1120 in the analyzer 1100.

For example, in the case where the detection chip 1200 is placed on the chip placement structure 1120, the photoelectric detector unit 1131 corresponding to the calibration area 1207 can receive the reflected light, so that the photoelectric detector unit 1131 outputs an electrical signal, thereby determining that a detection chip 1200 is in the analyzer 1100 at this time, the controller device can control the detection work of other photoelectric detector units 1131 according to the electrical signal. Conversely, in the case where the detection chip 1200 is not placed on the chip placement structure 1120, the photoelectric detector unit 1131 corresponding to the calibration area 1207 can receive the reflected light with very weak intensity, so that the photoelectric detector unit 1131 has no electrical signal output, thereby determining that no detection chip 1200 is in the analyzer 1100 under this case, and the analyzer 1100 does not perform detection.

Detection test paper placement areas 1208 are arranged in the plurality of detection area 1206, and detection test papers are placed in the detection test paper placement areas 1208, respectively. In addition, detection through holes 1209 are arranged at the center of the plurality of detection areas 1206, respectively. The liquid to be detected enters the plurality of detection area 1206 and reacts with the detection test paper 1208 through the detection through holes 1209, the degree of the color reaction can be observed, thereby judging whether the liquid to be detected is evenly distributed in the plurality of detection area 1206. In addition, the detection through holes 1209 can also contain excess liquid to be detected.

For example, in some examples, as shown in FIG. 12B, the plurality of detection areas 1206 of the detection chip 1200 is in a diamond shape. For example, the shape of the detection area 1206 may also include a circle shape, an ellipse shape, or a triangle shape. The embodiments of the present disclosure is not limited by the shape of the plurality of detection areas 1206.

For example, in some examples, as shown in FIG. 12A, the detection chip 1200 further includes a sample injection unit 1204. For example, the sample injection unit includes a through hole in the center and is in a petal shape. The through hole of the sample injection unit 1204 is connected with the sample injection opening 1202 of the cover plate 1201, and the liquid to be detected is dropped into the sample injection unit 1204, after that, the detection liquid passes through the sample injection opening 1202 of the cover plate 1201, enters the detection area 1206 of the detection chip through the micro-flow channel 1205, and undergoes a color reaction with the detection test paper 1208.

For example, in examples of other embodiments, as shown in FIG. 12C, the sample injection unit 1204 may also be in a cylindrical shape. The embodiments of the present disclosure are not limited to the specific shape of the sample injection unit.

For example, in other examples, the number of the plurality of detection areas 1206, for example, may also be two, three, four, six, seven, etc., which are not limited in the embodiments of the present disclosure.

For example, the calibration area 1207 in the detection chip is not necessary, and the detection chip may not be arranged with the calibration area 1207. As shown in the example of FIG. 12C, the detection chip includes six detection areas 1206, and no calibration area 1207 is arranged.

For example, in some examples, as shown in FIG. 12C, detection light through holes 1210 are arranged at positions of the substrate 1203 opposite to the detection through holes 1209 of the cover plate 1202, which allow the light emitted by the photoelectric detector units 1131 in the analyzer 1100 to enter the detection chip 1200 and the light reflected by the detection chip 1200 to be transmitted to the photoelectric detector units 1131.

Figure 13:
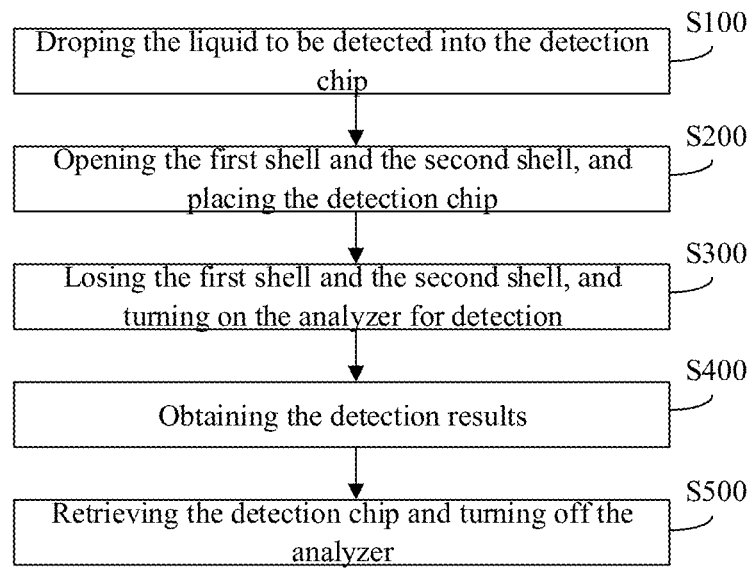
FIG. 13 is a schematic diagram of a detection process of the analyzer provided by at least one embodiment of the disclosure.

For example, in some examples, the analyzer shown in FIG. 1A and FIG. 1B is configured to detect the substance content of the liquid, and the detection process includes the steps shown in FIG. 13.

Step S100: dropping the liquid to be detected into the detection chip. After that the liquid to be detected is evenly distributed in the plurality of detection areas 1206 and the color reaction is completed, the detection chip 1200 can be subsequently placed in the analyzer 1100.

Step S200: opening the first shell and the second shell, and placing the detection chip. The opening distance (the second end portion 1194 of the first locking tongue 1183 and the second end portion 1195 of the second locking tongue 1184 are moved closer to the middle of the two) between the second end portion 1194 of the first locking tongue 1183 and the second end portion 1195 of the second locking tongue 1184 is reduced, the first end portion 1185 of the first locking tongue 1183 and the first end portion 1186 of the second locking tongue 1184 are separated from the locker 1188 in a state of being snapped with the locker 1188, so that the first shell 1110 and the second shell 1160 of the analyzer 1100 are opened, and the detection chip 1200 is placed in the chip placement structure 1120. The embodiments of the present disclosure are not limited to the sequence of step S100 and step S200, for example, after that the detection chip 1200 is placed in the chip placement structure 1120, the liquid to be detected is then dropped into the detection chip 1200, which is not specifically limited herein.

Step S300: closing the first shell and the second shell, and turning on the analyzer for detection. Closing the first shell 1110 and the second shell 1160, then long time pressing the micro-switch 1305a, the analyzer 1100 starts to detect. The controller device 1310 receives the detection results of the photoelectric detector units 1131 and sends the detection results to the displayer device 1170.

Step S400: obtaining the detection results. After the detection of the analyzer 1100 is completed, the detection results are checked by pressing the micro-switch 1305b on the display screen, the detection results such as detection reports are also possible to be sent to other devices via bluetooth (for example, pushing detection reports to software or applets used by users).

Step S500: retrieving the detection chip and turning off the analyzer. Turning on the first shell 1110 and the second shell 1160 of the analyzer 1100 again, taking the detection chip 1200 out, then the first shell 1110 and the second shell 1160 are closed, and short time pressing the micro-switch 1305a to turn off the analyzer 1100.

The analyzer 1100 can measure the contents of various substances in liquid, such as breast milk, at the same time, the analyzer 1100 can display the detection results in a short period of time (for example, 2-3 minutes). The above-mentioned analyzer 1100 has the advantages of simple structure and convenient operation, and can be used as a small, hand-held home testing equipment, so that the users can complete the entire detection process at home, and the analyzer 1100 can realize real-time upload of detection results to, for example, the port of an application (APP) installed on a mobile terminal such as a mobile phone, and it is convenient to provide users with, such as the analysis of the substance content of breast milk, and to provide professional nutrition, dietary guidance and clinical advice based on the analysis results.

For the detection system and the analyzer in the above embodiments, because the detector unit of the analyzer includes a plurality of photoelectric detector units or at least one relatively rotatable photoelectric detector unit, the analyzer can detect the plurality of detection areas of the detection chip through the plurality of photoelectric detector units, so that the content of various substances in the liquid to be detected in the detection chip is detected.

Figure 14:
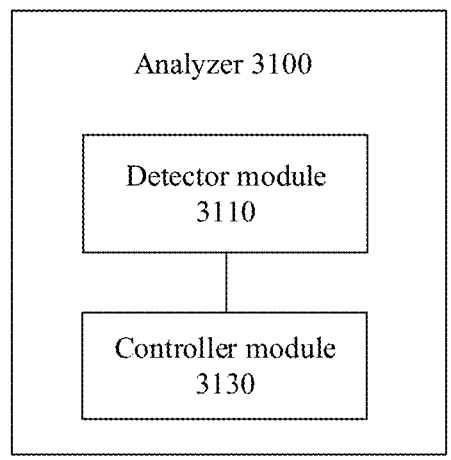
FIG. 14 is still another schematic diagram of the analyzer provided by at least one embodiment of the present disclosure.

FIG. 14 is still another schematic diagram of the analyzer provided by at least one embodiment of the present disclosure. The embodiments of the present disclosure further provide an analyzer, and the embodiments of the present disclosure may also be illustrated as shown in FIG. 14.

As shown in FIG. 14, the analyzer 3100 includes a detector module 3110 and a controller module 3130. The detector module 3110 includes a chip placement structure 3120. The detector module 3110 is configured to detect at least one detection area 1206 of the detection chip 1200 in the case where the detection chip 1200 (as shown in FIG. 12B) includes at least one detection area 1206 is placed on the chip placement structure 3120. The controller module 3130 is connected in signal with the detector module 3110, and is configured to control the detection operation of the detector module 3110 and receive the detection results of the detector module 3110.

For example, in some examples, the chip placement structure 3120 is a space in which the detection chip 1200 is placed, and the detection chip 1200 can be shielded from ambient light in the case where the detection chip 1200 is detected. For example, the chip placement structure 3120 may be the structure as shown in FIG. 2, in the case where the detector module 3110 includes the first shell 1110 and the second shell 1160, the chip placement structure 3120 is located in the first shell 1110, for placing the detection chip 1200. The first shell 1110 and the second shell 1160 can be opened and closed on one side, to facilitate the users to place and retrieve the detection chip 1200, and in the case where the analyzer 3100 is working, the interference of external light on the detection of the detection chip is avoided. The chip placement structure 3120 is a lower "concave" accommodating space formed in the first shell 1110 from the opening (for example, the circular opening 1301a of the first shielding plate 1301 in FIG. 2) in the upper surface (for example, formed by the surface of the first shielding plate 1301 in FIG. 2) of the first shell 1110. For example, a cross section of the accommodating space is substantially in a circular shape. It should be noted that, other shapes, such as rectangular, elliptical, etc., may also be adopted. In the case where the detector module 3110 only includes the first shell 1110, the upper surface of the first shell 1110 is made into a plane that can shield light, an opening is arranged at the side of the first shell 1110, and the opening is connected with the chip placement structure 3120. An object stage can be added to the chip placement structure 3120, the object stage can be ejected from the opening of the chip placement structure 3120 to place the detection chip 1200 on the object stage, and then the object stage is pushed into the chip placement structure 3120 to detect the detection chip 1200. It should be noted that, a drawer type can be selected for the operation of the object stage, and the ambient light is shielded in the case where the detection chip 1200 is detected.

For example, in some examples, the controller module 3130 receives the electrical signals sent by the detector module 3110, and obtains the detection results according to the electrical signals. For example, the controller device 3130 may include a processor and a memory, the processor may include a central processor unit (CPU), or a data processor (DSP), and the memory may include a semiconductor memory, which is configured to store computer codes for execution on the processor and to store data.

Figure 15:
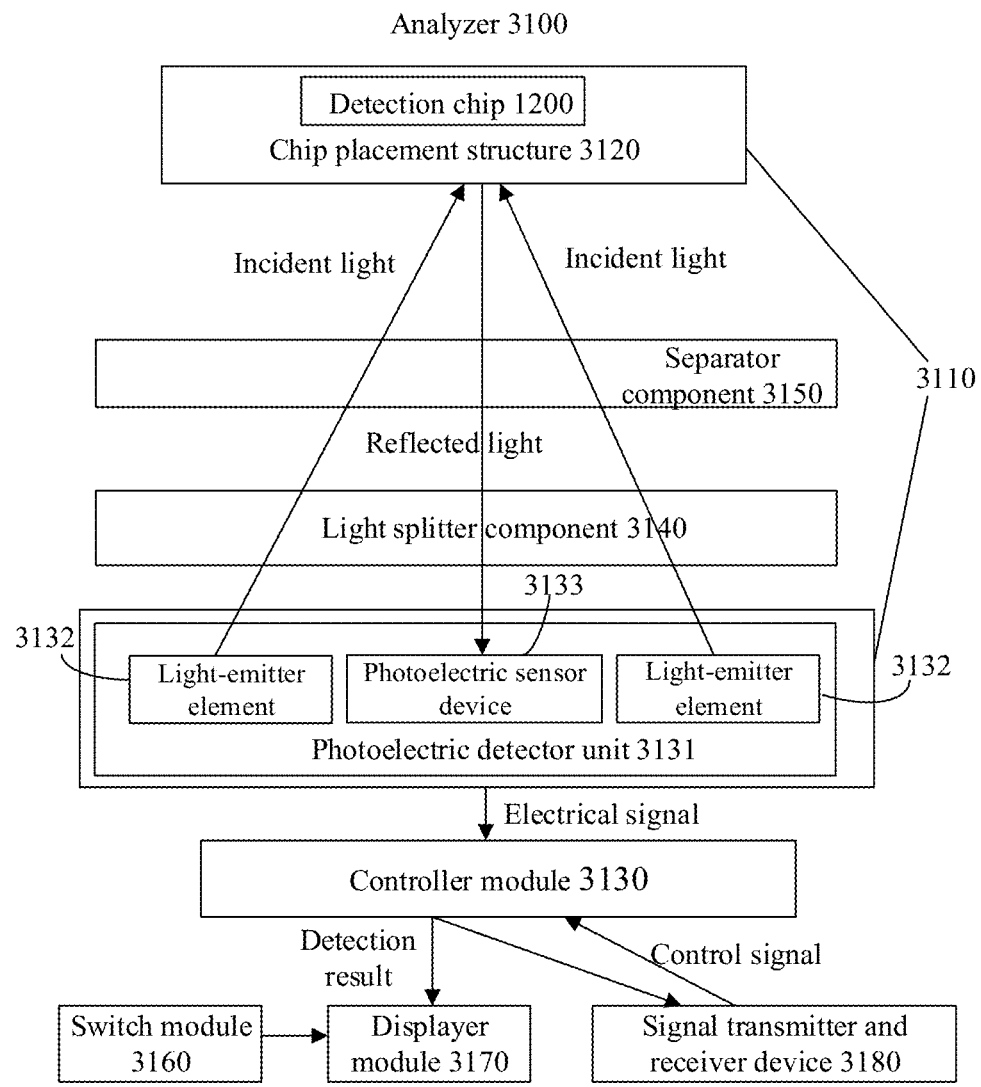
FIG. 15 is still another schematic diagram of the analyzer provided by at least one embodiment of the present disclosure.

FIG. 15 is still another schematic diagram of the analyzer provided by at least one embodiment of the present disclosure. As shown in FIG. 15, the detector module 3110 includes at least one photoelectric detector unit 3131. The at last one photoelectric detector unit 3131 may be of various types, for example, including but not limited to at lase one photoelectric detector unit 3131. These photoelectric detector units 3131 are configured to detect the plurality of detection areas 1206 of the detection chip 1200 in the case where the detection chip 1200 is placed on the chip placement structure 3120.

For example, in other examples, the detector module 3110 includes a plurality of photoelectric detector units 3131, the plurality of photoelectric detector units 3131 correspond to the plurality of detection areas 1206 of the detection chip 1200 (for example, in the vertical direction, that is, in the axial direction of the first shell 1110) respectively.

For example, in some examples, each of the photoelectric detector unit 3131 includes at least one light-emitter element and at least one photoelectric sensor device. As shown in FIG. 15, each of the plurality of photoelectric detector units 3131 includes two light-emitter elements 3132 and a photoelectric sensor device 3133. For example, the two photoelectric light-emitter elements 3132 (for example, symmetrical) are located at both sides of a photoelectric sensor device 3133. The arrangement of two light-emitter elements 3132 and one photoelectric sensor device 3133 can ensure that the light emitted by the light-emitter element 3132 is evenly incident on corresponding detection area of the detection chip 1200, and can also increase the intensity of the incident light provided by the two light-emitter elements 3132 and the intensity of the reflected light after being reflected by the detection chip 1200, thereby improving the stability of analyzer detection. For example, light of a specific intensity (incident light) emitted by the light-emitter element 3132 is transmitted to the chip placement structure 3120 to reach the detection chip 1200 placed on the chip placement structure 3120, then the light reflected by the plurality of detection areas 1206 (the detection sample in the plurality of detection areas 1206) of the detection chip 1200 is received by the photoelectric sensor device 3133. The photoelectric sensor device 3133 will receive light signals (reflected light) and convert the light signals into electrical signals. The controller device 3130 can obtain the intensity of the light signal received by the photoelectric sensor device 3133 according to the electrical signals.

For example, in other examples, each of the plurality of photoelectric detector units 3131 may also include a photoelectric sensor device 3133 and a light-emitter element 3132, and can also realize the detection of the liquid to be detected in the plurality of detection areas 1206 of the detection chip 1200. Alternatively, each of the plurality of photoelectric detector units 3131 may also include the plurality of photoelectric sensor devices 3133 and the plurality of light-emitter elements 3132, the plurality of photoelectric sensor devices 3133 can detect different substances in the liquid to be detected. The embodiments of the present disclosure are not limited by the number of light-emitter elements 3132 and the number of photoelectric sensor devices 3133.

For example, in some examples, the light-emitter element 3132 includes a light-emitting diode (Light-emitting Diode, LED), the photoelectric sensor device 3133 includes a photo-diode (PD), such as a silicon photo-diode. The Light-emitting diode can emit light of specific wavelength (for example, infrared light, red light, green light, etc.), and the light-emitting diode of specific wavelength can be selected according to the type of substance to be detected. The wavelengths of light emitted by light-emitting diodes located in different photoelectric detector units 3131 are different, so that the plurality of photoelectric detector units 3131 can detect various substances. For example, a photoelectric detector unit 3131 can select a light-emitter element that emits light with a wavelength of 630 nm, which is configured to detect the content of lactose and fat in the liquid to be detected, and the maximum absorption peak of light with a wavelength of 630 nm can be obtained, so that the photoelectric detector unit 3131 obtains the maximum receiving efficiency, thereby improving the accuracy of detection. For example, the photoelectric detector unit 3131 can also select a light-emitter element that emits light with a wavelength of 660 nm, which is configured to detect the content of calcium and protein in the liquid to be detected, and the maximum absorption peak of light with a wavelength of 660 nm can be obtained, so that the photoelectric detector unit 3131 obtains the maximum receiving efficiency, thereby improving the accuracy of detection. The photoelectric detector unit 3131 can also select a light-emitter element that emits light with a wavelength of 585 nm, which is configured to detect the content of zinc in the liquid to be detected, and the maximum absorption peak of light with a wavelength of 585 nm can be obtained, so that the photoelectric detector unit 3131 obtains the maximum receiving efficiency, thereby improving the accuracy of detection. In this way, the photoelectric sensor device 3133 of the photoelectric detector unit 3131 of the analyzer 3100 provided in the embodiments of the present disclosure can generate at least five detection signals (for example, corresponding to lactose, fat, zinc, calcium, and protein, respectively). The detector module 3110 can transmit a plurality of detection signals to the controller module 3130, the controller module 3130 processes the detection signals to obtain corresponding detection results, and the controller module 3130 may transmit the detection results to the displayer module 3170 (as shown in FIG. 15, the displayer module 3170 will be described in detail in the following) for display on the displayer module 3170. Therefore, the analyzer 3100 provided by the embodiments of the present disclosure can detect a plurality of index items (such as the content of lactose, fat, zinc, calcium, and protein) at the same time.

For example, in some examples, as shown in FIG. 15, the analyzer 3100 further includes a light splitter component 3140. The light splitter component 3140 is arranged between the chip placement structure 3120 and the at least one photoelectric detector unit 3131, and is configured as that the light emitted by the at least one light-emitter element 3132 is transmitted to the chip placement structure 3120, and the light reflected from the detection chip 1200 placed on the chip placement structure 3120 is transmitted to at least one photoelectric sensor device 3133. As shown in FIG. 6A, the light splitter component 3140 may include a light splitter disk 1141. The light splitter disk 1141 includes at least one group of light through holes 1142, and the at least one group of light through holes 1142 are evenly arranged on the same circumference of the light splitter disk 1141. Each group of light through holes 1142 includes at least one light-emitting through hole and at least one light-reflecting through hole, the at least one light-emitting through hole allows the light emitted by the light-emitter element 3132 of the corresponding photoelectric detector unit 3131 to pass through, and the at least one light-reflecting through hole allows light reflected from the detection chip 1200 placed on the chip placement structure 3120 to pass through for transmission to the photoelectric sensor device 3133 of the corresponding photoelectric detector unit 3131. Two light-emitting through holes 1143 are located at both sides of the light-reflecting through hole 1144, the light-emitting through holes 1143 corresponds to the light-emitter elements 3132 in the photoelectric detector unit 3131, and the light-reflecting through hole 1144 corresponds to the photoelectric sensor device 3133 in the photoelectric detector unit 3131. The light emitted by the light-emitter elements 3132 passes through the light-emitting through hole 1143 and then is incident on the chip placement structure 3120, and the light reflected from the detection chip 1200 placed on the chip placement structure 3120 passes through the light-reflecting through hole 1144 and then is received by the photoelectric sensor device 3133. The arrangement of the light splitter disk 1141 can avoid the interference of light signals between different photoelectric detector units 3131 to ensure the reliability of the detection results.

It should be noted that, the light splitter disk 1141 is an example of the light splitter component 3140, and the light splitter component 3140 can also be selected as other optical path structures, which is not limited in the embodiments of the present disclosure.

For example, in some examples, as shown in FIG. 15, the analyzer 3100 further includes a separator component 3150. The separator component 3150 is arranged between the light splitter component 3140 and the chip placement structure 3120. The separator component 3150 includes a light-transmitter portion. The light-transmitter portion is configured to allow the light emitted by the at least one light-emitter element 3132 and the light reflected from the detection chip 1200 placed on the chip placement structure 3120 to pass through. The separator component 3150 may include the separator component 1150 as shown in FIG. 4A. The separator component 1150 includes a light-transmitter portion 1151, which is configured to allow the light emitted by the light-emitter element 3132 of the photoelectric detector unit 3131 and the light reflected from the detection chip 1200 placed on the chip placement structure 3120 to pass through. The detection chip 1120 is located above the separator component 3150, and the separator component 3150 is configured to prevent the penetration of the liquid to be detected in the plurality of detection areas of the detection chip 1120, for example, the separator component 3150 can also provide protection functions for the optical path components below. The light-transmitter portion 1151 of the separator component 3150 includes at least one transparent window 1152, which respectively correspond to the plurality of photoelectric detector units 3131, so that the at least one transparent window 115 respectively allow the light emitted from the at least one light-emitter element 3132 of the corresponding photoelectric detector unit 3131 and the light reflected from the detection chip 1200 placed on the chip placement structure 3120 to the at least one photoelectric sensor device 3133 of the corresponding photoelectric detector unit 3131 to pass through.

For example, in some examples, as shown in FIG. 15, the analyzer 3100 further includes a displayer module 3170. The displayer module 3170 is connected in signal with the controller module 3130, and is configured to receive the detection results of the detector module 3110 sent by the controller module 3130 and to display the detection results of the detector module 3110. The displayer module 3170 may include, for example, a liquid crystal displayer device, an organic light-emitting diode (OLED) displayer device, electronic paper, a digital tube, etc., for displaying the detection results of the analyzer 3100. In the case where the analyzer 3100 includes the second shell 1160 or the first shell 1110 (as shown in FIG. 1), the displayer module 3170 may be arranged at the second shell 1160 or the first shell 1110.

For example, in some examples, as shown in FIG. 15, the analyzer 3100 further includes a switch module 3160. The switch module 3160 is connected in signal with the displayer module 3170, and is configured to control the content displayed on the displayer module 3170. The switch module 3160 can also realize the switch function of the analyzer 3100. For example, as shown in FIG. 9, the switch module 3160 can include a micro-switch 1305a and a micro-switch 1305b or one of the micro-switch 1305a and the micro-switch 1305b, which realizes the switch function of the analyzer 3100 and the function of controlling the display of the detection results on the displayer module 3170. For example, long time pressing the micro-switch 1305a to turn on the analyzer 1100, and to start the detection of the detection chip 1200, short time pressing the micro-switch 1305a to turn off the analyzer. The display contents of the displayer module 3170 is controlled by pressing the micro-switch 1305b, and the detection results can be viewed on the displayer module 3170 according to the selection.

For example, in some examples, as shown in FIG. 15, the analyzer 3100 further includes a signal transmitter and receiver device 3180. The signal transmitter and receiver device 3180 is connected with the controller module 3130, and is configured to upload the detection results of the detector unit 3110 to the mobile device, or configured to receive a control signal from the mobile device, and to transmit the control signal to the controller module 3130, to control the operation of the analyzer 3100. The signal transmitter and receiver device 3180 includes, for example, an antenna, a modem, etc., for communication, for example, using Bluetooth, WIFI, mobile communication (such as 2G/3G/4G/5G, etc.) to communicate, so that the detection results can be sent to other devices (for example, mobile terminals such as mobile phones, tablets, etc., or servers, etc.), for example, the detection results are uploaded to applications (APP) installed on mobile terminals such as mobile phones in real time; or control signals received from other devices are used to control the operation of the analyzer 3100 by the controller device, for example, it is possible to cooperate with the analyzer 1100 by installing an application program (APP) on a mobile terminal such as a mobile phone.

The following statements should be noted:
(1) The accompanying drawings involve only the structure(s) in connection with the embodiment(s) of the present disclosure, and other structure(s) can be referred to common design(s).
(2) In case of no conflict, the embodiments of the present disclosure and the features in the embodiments can be combined with each other to obtain new embodiments.

The above are merely specific implementations of the present disclosure without limiting the protection scope of the present disclosure thereto. The protection scope of the present disclosure should be based on the protection scope of the appended claims.

What is claimed is:

1. An analyzer, comprising:
   a chip placement structure, configured to place a detection chip, wherein the detection chip is provided with at least one detection area, and
   at least one detector unit, comprising at least one photoelectric detector unit, each of the at least one photoelectric detector unit comprises at least one light-emitter element and at least one photoelectric sensor device,
   wherein the at least one detector unit is configured to detect one detection area or more detection areas of the detection chip in a case where the detection chip is placed on the chip placement structure,
   the analyzer further comprising:
      an optical path component, wherein the optical path component is provided between the chip placement structure and the detector unit, and the optical path component is configured to transmit light emitted by the at least one light-emitter element to the chip placement structure and transmit light reflected from the detection chip placed on the chip placement structure to the at least one photoelectric sensor device,
      the optical path component comprises a light splitter disk, the light splitter disk comprises at least one group of light through holes, and the at least one group of light through holes corresponds to the at least one photoelectric detector unit respectively, and
      each group of the at least one group of light through holes comprises at least one light-emitting through hole and at least one light-reflecting through hole, the at least one light-emitting through hole allows the light emitted by the at least one light-emitter element of corresponding photoelectric detector unit to pass through, and the at least one light-reflecting through hole allows the light reflected from the detection chip placed on the chip placement structure to pass through so as to transmit to the at least one photoelectric sensor device of the corresponding photoelectric detector unit.

2. The analyzer according to claim 1, wherein
   each group of the at least one group of light through holes comprises two light-emitting through holes and one light-reflecting through hole, and the two light-emitting through holes are provided at two opposite sides of the one light-reflecting through hole.

3. The analyzer according to claim 2, wherein
   the one light-reflecting through hole of each group of the at least one group of the light through holes comprises a first reflecting through sub-hole located at a side of the light splitter disk facing away from the at least one detector unit and a second reflecting through sub-hole located at a side of the light splitter disk close to the at least one detector unit, and
   a diameter of the first reflecting through sub-hole is smaller than a diameter of the second reflecting through sub-hole.

4. The analyzer according to claim 2, wherein
   a surface of the light splitter disk at a side facing away from the at least one detector unit comprises at least one protrusion, and the at least one protrusion protrudes obliquely to the side facing away from the at least one detector unit along a direction from a side of the two light-emitting through holes of each group of the at least one group of light through holes close to the one light-reflecting through hole to a side close to the one light-reflecting through hole, and
   the one light-reflecting through hole of the at least one group of the light through holes is located in the at least one protrusion in a one-to-one correspondence, so that the protrusion shields light emitted from the at least one light-emitter element of corresponding photoelectric detector unit through the light-emitting through hole.

5. The analyzer according to claim 2, wherein
   each of the at least one photoelectric detector unit comprises two light-emitter elements and one photoelectric sensor device, and the two light-emitter elements are provided at two opposite sides of the one photoelectric sensor device; and
   the two light-emitting through holes respectively allow the light emitted by the two light-emitter elements to pass through respectively, and the one light-reflecting through hole allows the light reflected from the detection chip placed on the chip placement structure to pass through so as to transmit to the one photoelectric sensor device.

6. The analyzer according to claim 5, further comprising:
   a separator component, wherein
   the separator component is provided between the optical path component and the chip placement structure, and
   the separator component comprises a light-transmitter portion, and the light-transmitter portion is configured to allow light emitted by the at least one light-emitter element and light reflected from the detection chip placed on the chip placement structure to pass through.

7. The analyzer according to claim 6, further comprising:
   a detection circuit board, wherein
   the photoelectric detector unit is provided on the detection circuit board, and the detection circuit board comprises a first positioning hole,
   the separator component comprises a positioning pin and the light splitter disk comprises a second positioning hole, or the separator component comprises a second positioning hole and the light splitter disk comprises a positioning column, and
   the positioning column penetrates both the first positioning hole and the second positioning hole to connect the light splitter disk, the separator component, and the detection circuit board.

8. The analyzer according to claim 1, further comprising:
   a rotation driver device, wherein
   in the case where only one detector unit is provided, the rotation driver device is configured to drive the one detector unit to rotate with respect to the chip placement structure.

9. The analyzer according to claim 1, further comprising:
   a first shell and a second shell, wherein the at least one detector unit is provided in a space enclosed by the first shell and the second shell, wherein
   the second shell is hinged with the first shell at a first side,
   the second shell is configured to be closed with the first shell at a second side to enclose the chip placement structure and is configured to be opened at the second side to expose the chip placement structure, and
   the first side is opposite to the second side.

10. The analyzer according to claim 9, wherein
    the first shell comprises a first opening and closing sub-component provided at the second side,
    the second shell comprises a second opening and closing sub-component provided at the second side, the first opening and closing component and the second opening and closing sub-component are configured to be combined with each other to close the first shell and the second shell with each other and configured to be separated from each other to open the first shell and the second shell with each other, the second opening and closing sub-component comprises a first locking tongue in a long strip shape and a second locking tongue in a long strip shape, the first locking tongue and the second locking tongue are provided side by side in a pair, the first opening and closing sub-component comprises a groove and a locker, and the locker is located in the groove, and a first end portion of the first locking tongue and a first end portion of the second locking tongue are configured to extend into the groove and to be snapped with the locker so that the first shell and the second shell are closed, and the first shell and the second shell are configured to be separated from the locker so that the first shell and the second shell are opened.

11. The analyzer according to claim 10, further comprising:
a displayer device, provided at the second shell.

12. The analyzer according to claim 11, further comprising:
at least one micro-switch, connected in signal with the displayer device, wherein the at least one micro-switch is configured to control contents displayed on the displayer device, wherein
the at least one micro-switch comprises two micro-switches,
one micro-switch of the two micro-switches is provided at the first end portion of the first locking tongue and is configured to control a switch of the analyzer,
the other micro-switch of the two micro-switches is provided at the first end portion of the second locking tongue and is configured to control display of detection results of the analyzer on the displayer device.

13. The analyzer according to claim 11, further comprising:
a controller device, connected in signal with the detector unit and the displayer device, wherein the controller device is configured to receive detection results of the detector unit and send the detection results to the displayer device, and the displayer device is configured to display the detection results.

14. The analyzer according to claim 13, further comprising:
a signal transmitter and receiver device, wherein the signal transmitter and receiver device is connected with the controller device, and the signal transmitter and receiver device is configured to upload the detection results to a mobile device, or is configured to receive control signals from the mobile device and transmit the control signals to the controller device to control an operation of the analyzer.

15. The analyzer according to claim 13, further comprising:
a temperature sensor and a humidity sensor, wherein
the temperature sensor and the humidity sensor are respectively connected with the controller device,
the temperature sensor is configured to detect environmental temperature and to upload a temperature detection data to the controller device, and
the humidity sensor is configured to detect environmental humidity and to upload a humidity detection data to the controller device.

16. A detection system, comprising:
the analyzer according to claim 1, and
a detection chip, configured to be placed on the chip placement structure of the analyzer.

* * * * *